(12) United States Patent
An et al.

(10) Patent No.: US 12,161,484 B2
(45) Date of Patent: Dec. 10, 2024

(54) DISPLAY DEVICE AND BLOOD PRESSURE MEASUREMENT METHOD USING THE SAME

(71) Applicant: Samsung Display Co., LTD., Yongin-si (KR)

(72) Inventors: Jong Yeop An, Yongin-si (KR); Gyeong Ub Moon, Yongin-si (KR); Hyeon Jun Lee, Yongin-si (KR); Bo Ram Choi, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 196 days.

(21) Appl. No.: 17/989,543

(22) Filed: Nov. 17, 2022

(65) Prior Publication Data

US 2023/0346315 A1     Nov. 2, 2023

(30) Foreign Application Priority Data

Apr. 29, 2022 (KR) .......................... 10-2022-0053394

(51) Int. Cl.
    *A61B 5/00*              (2006.01)
    *A61B 5/021*            (2006.01)
    *A61B 5/024*            (2006.01)

(52) U.S. Cl.
    CPC ........ *A61B 5/6898* (2013.01); *A61B 5/02116* (2013.01); *A61B 5/02125* (2013.01);
(Continued)

(58) Field of Classification Search
None
See application file for complete search history.

(56) References Cited

U.S. PATENT DOCUMENTS 9,049,998 B2    6/2015    Brumback et al.
2016/0213331 A1*    7/2016    Gil .......................... A61B 5/389
(Continued)

FOREIGN PATENT DOCUMENTS

| CN | 108652605 A | 10/2018 |
|---|---|---|
| KR | 10-2019-0105421 A | 9/2019 |
| KR | 10-2020-0095891 A | 8/2020 |

OTHER PUBLICATIONS

Chen et al., "Development of a Portable All-Wavelength PPG Sensing Device for Robust Adaptive-Depth Measurement: A Spectrometer Approach with a Hydrostatic Measurement Example," (Nov. 17, 2020), Sensors 2020, 20, 6556. (Year: 2020).*

(Continued)

*Primary Examiner* — Joel Lamprecht
*Assistant Examiner* — Ashish S Jasani
(74) *Attorney, Agent, or Firm* — Lewis Roca Rothgerber Christie LLP

(57) ABSTRACT

A blood pressure measurement method using a display device including: a display panel including first sub-pixels and second sub-pixels; a pressure sensor to sense a pressure applied from the outside; and a photo-sensor to sense light, includes: generating a first pulse wave signal according to light emitted by the first sub-pixels and sensed by the photo-sensor; generating a second pulse wave signal according to light emitted by the second sub-pixels and sensed by the photo-sensor; generating a third pulse wave signal by removing noise from the second pulse wave signal based on the first pulse wave signal, the second pulse wave signal, and a maximum value of the first pulse wave signal; and calculating blood pressure information based on the third pulse wave signal and a pressure measurement value sensed by the pressure sensor. The blood pressure information is displayed on the display panel.

20 Claims, 29 Drawing Sheets

(52) U.S. Cl.
CPC .......... *A61B 5/6826* (2013.01); *A61B 5/6843* (2013.01); *A61B 5/7203* (2013.01); *A61B 5/742* (2013.01); *A61B 5/02427* (2013.01); *A61B 2562/0247* (2013.01)

(56) References Cited

U.S. PATENT DOCUMENTS

| | | | |
|---|---|---|---|
| 2019/0239758 A1* | 8/2019 | Park | A61B 5/6843 |
| 2019/0302937 A1* | 10/2019 | Heo | G06F 1/1652 |
| 2020/0113453 A1* | 4/2020 | Park | A61B 5/02416 |
| 2020/0121259 A1* | 4/2020 | Shin | A61B 5/486 |
| 2021/0085259 A1* | 3/2021 | Kwon | A61B 5/024 |
| 2024/0000326 A1* | 1/2024 | Mahajan | A61B 5/0077 |

OTHER PUBLICATIONS

Chandrasekar et al., "Smartphone-based blood pressure monitoring via the oscillometric finger-pressing method," (Mar. 7, 2018), Sci Transl Med. Mar. 7, 2018; 10(431). (Year: 2018).*
Liu, Jing, et al., "Non-Invasive Capillary Blood Pressure Measurement Enabling Early Detection and Classification of Venous Congestion", IEEE Journal of Biomedical and Health Informatics, 2021, IEEE, 10 pages.
Han, Sangjin, et al., "Design of Multi-Wavelength Optical Sensor Module for Depth-Dependent Photoplethysmography", Sensors, 2019, pp. 1-11, vol. 19, 11 pages.

\* cited by examiner

PX: PX1, PX2, PX3, PX4

DISPLAY DEVICE AND BLOOD PRESSURE MEASUREMENT METHOD USING THE SAME

CROSS-REFERENCE TO RELATED APPLICATION

This application claims priority to and the benefit of Korean Patent Application No. 10-2022-0053394, filed on Apr. 29, 2022, in the Korean Intellectual Property Office, the entire content of which is incorporated by reference herein.

BACKGROUND

1. Field

Aspects of embodiments of the present disclosure relate to a display device, and a blood pressure measurement method using the display device.

2. Description of the Related Art

Display devices display screens, and have been used in televisions (TVs) and monitors, as well as in mobile smart-phones and tablet personal computers (PCs). Portable display devices are provided with various functions. Examples of such various functions include a camera function, a fingerprint sensor function, and the like.

The above information disclosed in this Background section is for enhancement of understanding of the background of the present disclosure, and therefore, it may contain information that does not constitute prior art.

SUMMARY

Recently, as the healthcare industry has attracted attention, methods for more conveniently acquiring biometric information regarding health have been developed. For example, it may be desirable to replace a traditional oscillometric pulse measurement device with an electronic product that may be conveniently carried. However, such an electronic pulse measurement device may include an independent light source, sensor, and a display in itself, and may be separately carried, which may be inconvenient.

One or more embodiments of the present disclosure are directed to a display device capable of extracting and blocking noise components for a user, and a blood pressure measurement method using the display device.

However, the aspects and features of the present disclosure are not restricted to those set forth herein. The above and other aspects and features of the present disclosure will become more apparent to those of ordinary skill in the art to which the present disclosure pertains by reviewing the detailed description of the present disclosure given below, with reference to the figures.

According to one or more embodiments of the present disclosure, a blood pressure measurement method using a display device including: a display panel including first sub-pixels to emit light of a first color, and second sub-pixels to emit light of a second color; a pressure sensor to sense a pressure applied from the outside; and a photo-sensor to sense light, includes: generating a first pulse wave signal according to light emitted by the first sub-pixels and sensed by the photo-sensor; generating a second pulse wave signal according to light emitted by the second sub-pixels and sensed by the photo-sensor; generating a third pulse wave signal by removing noise from the second pulse wave signal based on the first pulse wave signal, the second pulse wave signal, and a maximum value of the first pulse wave signal; and calculating blood pressure information based on the third pulse wave signal and a pressure measurement value sensed by the pressure sensor. The blood pressure information is displayed on the display panel.

In an embodiment, the generating of the third pulse wave signal may include: calculating a first maximum value of the first pulse wave signal and a second maximum value of the second pulse wave signal; and generating the third pulse wave signal based on a ratio of the second maximum value to the first maximum value.

In an embodiment, the third pulse wave signal may be generated according to $$PG3 = PG2 - \frac{K2}{K1}PG1,$$

where PG1 may be the first pulse wave signal, K1 may be the first maximum value, PG2 may be the second pulse wave signal, K2 may be the second maximum value, and PG3 may be the third pulse wave signal.

In an embodiment, the generating of the third pulse wave signal may include: calculating a first maximum value of the first pulse wave signal; calculating a first section of the first maximum value; calculating a third maximum value of the second pulse wave signal in the first section; and generating the third pulse wave signal based on a ratio of the third maximum value to the first maximum value.

In an embodiment, the third pulse wave signal may be generated according to $$PG3 = PG2 - \frac{K3}{K1}PG1,$$

where PG1 may be the first pulse wave signal, K1 may be the first maximum value, PG2 may be the second pulse wave signal, K3 may be the third maximum value, and PG3 may be the third pulse wave signal.

In an embodiment, a wavelength of the light of the first color emitted by the first sub-pixels may be smaller than a wavelength of the light of the second color emitted by the second sub-pixels.

In an embodiment, the light of the first color emitted by the first sub-pixels may be green light, and the light of the second color emitted by the second sub-pixels may be red light.

In an embodiment, the first sub-pixels and the second sub-pixels may be configured to alternately emit light with each other, and the photo-sensor may be configured to alternately sense the light emitted by the first sub-pixels and the light emitted by the second sub-pixels.

In an embodiment, the photo-sensor may include: a first photo-sensor area configured to sense the light of the first color emitted by the first sub-pixels; and a second photo-sensor area configured to sense the light of the second color emitted by the second sub-pixels, and the first sub-pixels and the second sub-pixels may be surrounded by the first photo-sensor area.

In an embodiment, the first photo-sensor area may be surrounded by the second photo-sensor area.

In an embodiment, the calculating of the blood pressure information may include: generating a fourth pulse wave signal based on the third pulse wave signal and the pressure measurement value; generating a peak detection signal based on peak values of the fourth pulse wave signal; calculating a pressure value corresponding to a peak value of the peak detection signal; and calculating a diastolic blood pressure lower than the pressure value, a systolic blood pressure higher than the pressure value, and a mean blood pressure according to the pressure value.

In an embodiment, a first pressure value smaller than the pressure value corresponding to 60% to 80% of the peak value in the peak detection signal may be calculated as the diastolic blood pressure, and a second pressure value greater than the pressure value may be calculated as the systolic blood pressure.

According to one or more embodiments of the present disclosure, a blood pressure measurement method using a display device including: a display panel including first sub-pixels to emit light of a first color, and second sub-pixels to emit light of a second color; a pressure sensor to sense a pressure applied from the outside; and a photo-sensor to sense light, includes: generating a first pulse wave signal by sensing, by the photo-sensor, light emitted by the first sub-pixels; generating a second pulse wave signal by sensing, by the photo-sensor, light emitted by the second sub-pixels; generating a first pulse wave frequency signal based on the first pulse wave signal, the first pulse wave frequency signal having a magnitude of a pulse wave signal according to a frequency; generating a second pulse wave frequency signal based on the second pulse wave signal, the second pulse wave frequency signal having a magnitude of a pulse wave signal according to a frequency; changing the first pulse wave signal based on the first pulse wave frequency signal and the second pulse wave frequency signal; generating a third pulse wave signal by removing noise from the second pulse wave signal based on the changed first pulse wave signal and the second pulse wave signal; and calculating blood pressure information based on the third pulse wave signal and a pressure measurement value sensed by the pressure sensor. The blood pressure information is displayed on the display panel.

In an embodiment, the blood pressure measurement method may further include calculating a first center frequency of first harmonics of the first pulse wave frequency signal, and calculating a second center frequency of second harmonics of the second pulse wave frequency signa. When the first center frequency and the second center frequency are different from each other, the first pulse wave frequency signal may be changed to coincide the first center frequency with the second center frequency.

In an embodiment, the generating of the third pulse wave signal may include: calculating a first maximum value of the first pulse wave signal; calculating a second maximum value of the second pulse wave signal; and generating the third pulse wave signal based on a ratio of the second maximum value to the first maximum value.

In an embodiment, the third pulse wave signal may be generated according to $$PG3 = PG2 - \frac{K2}{K1}PG1,$$

where PG1 may be the first pulse wave signal, K1 may be the first maximum value, PG2 may be the second pulse wave signal, K2 may be the second maximum value, and PG3 may be the third pulse wave signal.

In an embodiment, the calculating of the blood pressure information may include generating a fifth pulse wave signal based on the third pulse wave signal and the pressure measurement value, one cycle of the fifth pulse wave signal may include a plurality of waveforms having different amplitudes from one another, a peak value of a first waveform of the plurality of waveforms having a pulse wave contraction value SP, and a peak value of a second waveform of the plurality of waveforms having a reflected pulse wave value, and a reflected pulse wave ratio may be defined by $$RI = \frac{Rp}{Sp},$$

where RI may be the reflected pulse wave ratio, SP may be the pulse wave contraction value, and RP may be the reflected pulse wave value.

In an embodiment, the reflected pulse wave ratio may include a first period in which the reflected pulse wave ratio fluctuates within a first range, a second period in which the reflected pulse wave ratio fluctuates within a second range, and a third period in which the reflected pulse wave ratio fluctuates within a third range, and a width of the first range and a width of the third range may be smaller than a width of the second range.

In an embodiment, the reflected pulse wave ratio may be analyzed to detect a start point in time of the second period; a third pressure value corresponding to the first pulse wave signal at the start point in time of the second period may be calculated as a diastolic blood pressure; and a fourth pressure value corresponding to the first pulse wave signal at a start point in time of the third period after the second period may be calculated as a systolic blood pressure.

According to one or more embodiments of the present disclosure, a display device includes: a display panel including first sub-pixels to emit light of a first color, and second sub-pixels to emit light of a second color; a pressure sensor to sense a pressure applied from the outside; a photo-sensor to sense light; and a main processor to receive a pressure measurement value sensed by the pressure sensor, a first pulse wave signal generated by sensing, by the photo-sensor, light emitted by the first sub-pixels, and a second pulse wave signal generated by sensing, by the photo-sensor, light emitted by the second sub-pixels. The main processor is configured to: generate a third pulse wave signal by removing noise from the second pulse wave signal based on the first pulse wave signal, the second pulse wave signal, and a maximum value of the first pulse wave signal; and calculate blood pressure information based on the third pulse wave signal and the pressure measurement value.

According to one or more embodiments of the present disclosure, a blood pressure of a user may be measured by sensing light reflected from a blood vessel or the like of a finger of the user by a photo-sensor of a display panel, and analyzing a pulse wave signal according to an amount of the sensed light.

In more detail, when blood pressure calculation is inaccurate due to the presence of different noise components for a user in the pulse wave signal, accuracy of the blood pressure calculation may be improved by extracting and blocking the noise components for the user.

However, the aspects and features of the present disclosure are not limited to the aforementioned aspects and features, and various other aspects and features are included in the specification, for example, as described in more detail below, and/or as would be apparent to those having ordinary skill in the art by practicing one or more of the present embodiments of the present disclosure.

BRIEF DESCRIPTION OF THE DRAWINGS

The above and other aspects and features of the present disclosure will be more clearly understood from the following detailed description of the illustrative, non-limiting embodiments with reference to the accompanying drawings, in which.

DETAILED DESCRIPTION

Figure 1:
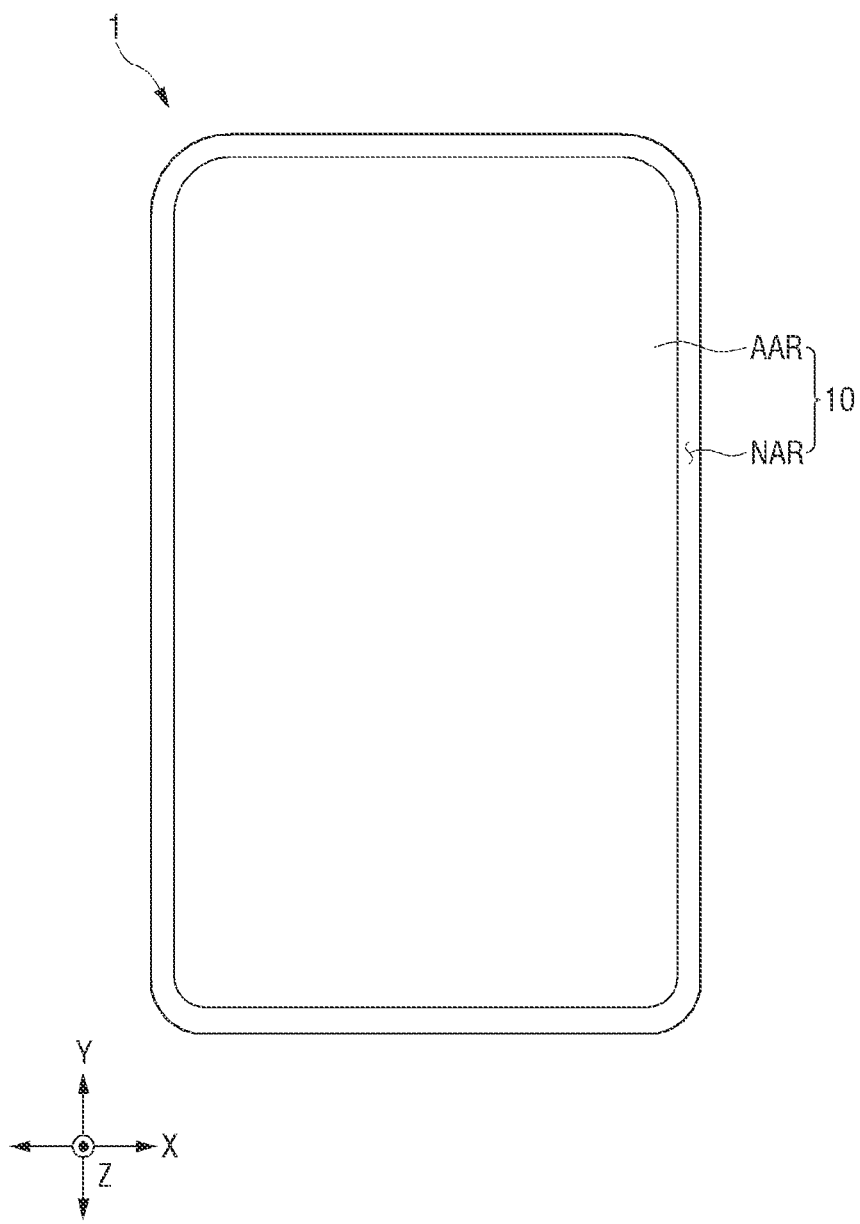
FIG. 1 is a plan view of a display device according to an embodiment.

Hereinafter, embodiments will be described in more detail with reference to the accompanying drawings, in which like reference numbers refer to like elements throughout. The present disclosure, however, may be embodied in various different forms, and should not be construed as being limited to only the illustrated embodiments herein. Rather, these embodiments are provided as examples so that this disclosure will be thorough and complete, and will fully convey the aspects and features of the present disclosure to those skilled in the art. Accordingly, processes, elements, and techniques that are not necessary to those having ordinary skill in the art for a complete understanding of the aspects and features of the present disclosure may not be described. Unless otherwise noted, like reference numerals denote like elements throughout the attached drawings and the written description, and thus, redundant description thereof may not be repeated.

When a certain embodiment may be implemented differently, a specific process order may be different from the described order. For example, two consecutively described processes may be performed at the same or substantially at the same time, or may be performed in an order opposite to the described order.

In the drawings, the relative sizes, thicknesses, and ratios of elements, layers, and regions may be exaggerated and/or simplified for clarity. Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

In the figures, the x-axis, the y-axis, and the z-axis are not limited to three axes of the rectangular coordinate system, and may be interpreted in a broader sense. For example, the x-axis, the y-axis, and the z-axis may be perpendicular to or substantially perpendicular to one another, or may represent different directions from each other that are not perpendicular to one another.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "on," "connected to," or "coupled to" another element or layer, it can be directly on, connected to, or coupled to the other element or layer, or one or more intervening elements or layers may be present. Similarly, when a layer, an area, or an element is referred to as being "electrically connected" to another layer, area, or element, it may be directly electrically connected to the other layer, area, or element, and/or may be indirectly electrically connected with one or more intervening layers, areas, or elements therebetween. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments and is not intended to be limiting of the present disclosure. As used herein, the singular forms "a" and "an" are intended to include the plural forms as well, unless the context clearly indicates otherwise. It will be further understood that the terms "comprises," "comprising," "includes," "including," "has," "have," and "having," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. For example, the expression "A and/or B" denotes A, B, or A and B. Expressions such as "at least one of," when preceding a list of elements, modify the entire list of elements and do not modify the individual elements of the list. For example, the expression "at least one of a, b, or c," "at least one of a, b, and c," and "at least one selected from the group consisting of a, b, and c" indicates only a, only b, only c, both a and b, both a and c, both b and c, all of a, b, and c, or variations thereof.

As used herein, the term "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

The electronic or electric devices and/or any other relevant devices or components according to embodiments of the present disclosure described herein (e.g., the pulse wave correction unit, the blood pressure calculation unit, the calculator, the corrector, the pulse wave signal generator, and/or the like) may be implemented utilizing any suitable hardware, firmware (e.g., an application-specific integrated circuit), software, or a combination of software, firmware, and hardware. For example, the various components of these devices may be formed on one integrated circuit (IC) chip or on separate IC chips. Further, the various components of these devices may be implemented on a flexible printed circuit film, a tape carrier package (TCP), a printed circuit board (PCB), or formed on one substrate. Further, the various components of these devices may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the spirit and scope of the example embodiments of the present disclosure.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Figure 2:
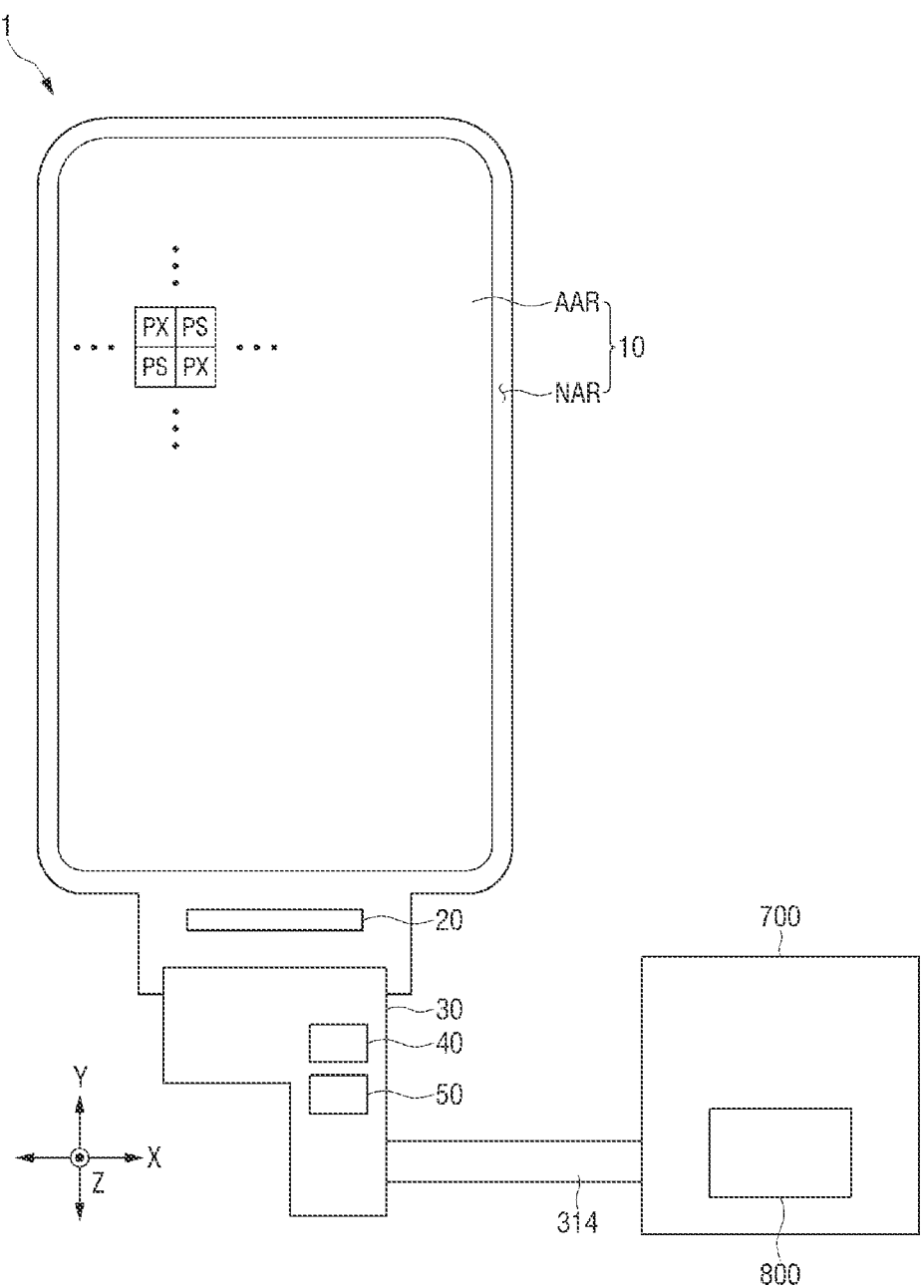
FIG. 2 is a plan view of the display device according to an embodiment.

FIG. 1 is a plan view of a display device according to an embodiment. FIG. 2 is a plan view of the display device according to an embodiment.

Referring to FIGS. 1 and 2, a display device 1 may include various suitable electronic devices for providing a display screen. Examples of the display device 1 may include, but are not limited to, mobile phones, smartphones, tablet personal computers (PCs), mobile communication terminals, electronic notebooks, electronic books, personal digital assistants (PDAs), portable multimedia players (PMPs), navigation devices, ultra mobile PCs (UMPCs), televisions, game machines, wrist watch-type electronic devices, head-mounted displays, monitors of personal computers, laptop computers, vehicle instrument boards, digital cameras, camcorders, external billboards, electric signs, various medical devices, various inspection devices, various home appliances including display areas, such as refrigerators and washing machines, Internet of Things (IoT) devices, and/or the like. Representative examples of the display device 1 described in more detail below may include smartphones, tablet PCs, laptop computers, and/or the like, but the present disclosure is not limited thereto.

The display device 1 may include a display panel 10, a display driver 20, a circuit board 30, a pulse wave sensing circuit 50, a pressure sensing circuit 40, a main circuit board 700, and a main processor 800.

The display panel 10 may include an active area AAR and a non-active area NAR.

The active area AAR includes a display area, in which a screen is displayed. The active area AAR may completely overlap with the display area. A plurality of pixels PX for displaying an image may be disposed at (e.g., in or on) the display area. Each pixel PX may include a light emitting unit (e.g., a light emitting element) for emitting light.

The active area AAR further includes a light sensing area. The light sensing area is an area for responding to light, and is an area configured to sense an amount, a wavelength, and/or the like of incident light. The light sensing area may overlap with the display area. In an embodiment, the light sensing area may completely overlap with the active area AAR in a plan view. In this case, the light sensing area and the display area may be the same or substantially the same area as each other. In another embodiment, the light sensing area may be disposed at (e.g., in or on) a portion (e.g., disposed only at the portion) of the active area AAR. For example, the light sensing area may be disposed at (e.g., in or on) a limited area used for fingerprint recognition. In this case, the light sensing area may overlap with a portion of the display area, but may not overlap with another portion of the display area.

A plurality of photo-sensors PS for responding to light may be disposed at (e.g., in or on) the light sensing area.

The non-active area NAR may be disposed around (e.g., adjacent to) the active area AAR. For example, the non-active area NAR may surround (e.g., around a periphery of) the active area AAR. The display driver 20 may be disposed at (e.g., in or on) the non-active area NAR. The display driver 20 may drive the plurality of pixels PX and/or the plurality of photo-sensors PS. The display driver 20 may output signals and voltages for driving the display panel 10. The display driver 20 may be formed as an integrated circuit (IC), and be mounted on the display panel 10. Signal lines for transferring signals between the display driver 20 and the active area AAR may be further disposed at (e.g., in or on) the non-active area NAR. As another example, the display driver 20 may be mounted on the circuit board 30.

The circuit board 30 may be attached to one end of the display panel 10 using an anisotropic conductive film (ACF). Lead lines of the circuit board 30 may be electrically connected to pad parts of the display panel 10. The circuit board 30 may be a flexible printed circuit board or a flexible film, such as a chip on film.

The pulse wave sensing circuit 50 may be disposed on the circuit board 30. The pulse wave sensing circuit 50 may be formed as an integrated circuit, and may be attached to an upper surface of the circuit board 30. The pulse wave sensing circuit 50 may be connected to a display layer of the display panel 10. The pulse wave sensing circuit 50 may sense a photocurrent generated by photocharges incident on the plurality of photo-sensors PS of the display panel 10. The pulse wave sensing circuit 50 may recognize a pulse wave of a user based on the photocurrent.

The pressure sensing circuit 40 may be disposed on the circuit board 30. The pressure sensing circuit 40 may be formed as an integrated circuit, and may be attached to the upper surface of the circuit board 30. The pressure sensing circuit 40 may be connected to the display layer of the display panel 10. The pressure sensing circuit 40 may sense electrical signals according to pressure applied to a plurality of pressure sensors of the display panel 10. The pressure sensing circuit 40 may generate pressure data according to a change in the electrical signal sensed by the pressure sensor, and may transmit the pressure data to the main processor 800.

The main circuit board 700 may be a printed circuit board or a flexible printed circuit board.

The main circuit board 700 may include the main processor 800.

The main processor 800 may control all functions of the display device 1. For example, the main processor 800 may output digital video data to the display driver 20 through the circuit board 30, so that the display panel 10 displays an image. In addition, the main processor 800 may receive touch data from a touch driving circuit, determine touch coordinates of the user, and execute an application indicated by an icon displayed at (e.g., in or on) the touch coordinates of the user.

The main processor 800 may calculate a pulse wave signal PPG reflecting a blood change depending on a heartbeat, according to an optical signal input from the pulse wave sensing circuit 50. In addition, the main processor 800 may calculate a touch pressure of the user, according to the electrical signal input from the pressure sensing circuit 40. Further, the main processor 800 may calculate a blood pressure of the user based on the pulse wave signal PPG and a pressure signal. In this case, the main processor 710 may calculate the blood pressure by blocking or reducing noise components generated for a user by a pulse wave correction unit (e.g., a pulse wave corrector) 810 (e.g., see FIG. 3). The pulse wave correction unit 810 will be described in more detail below.

The main processor 800 may be an application processor formed of an integrated circuit, a central processing unit, or a system chip.

In addition, a mobile communication module (e.g., a mobile communication device) capable of transmitting and receiving wireless signals to and from at least one of a base station, an external terminal, and a server over a mobile communication network may be further mounted on the main circuit board 700. The wireless signal may include various suitable kinds of data according to transmission/reception of a voice signal, a video call signal, or a text/multimedia message.

Figure 3:
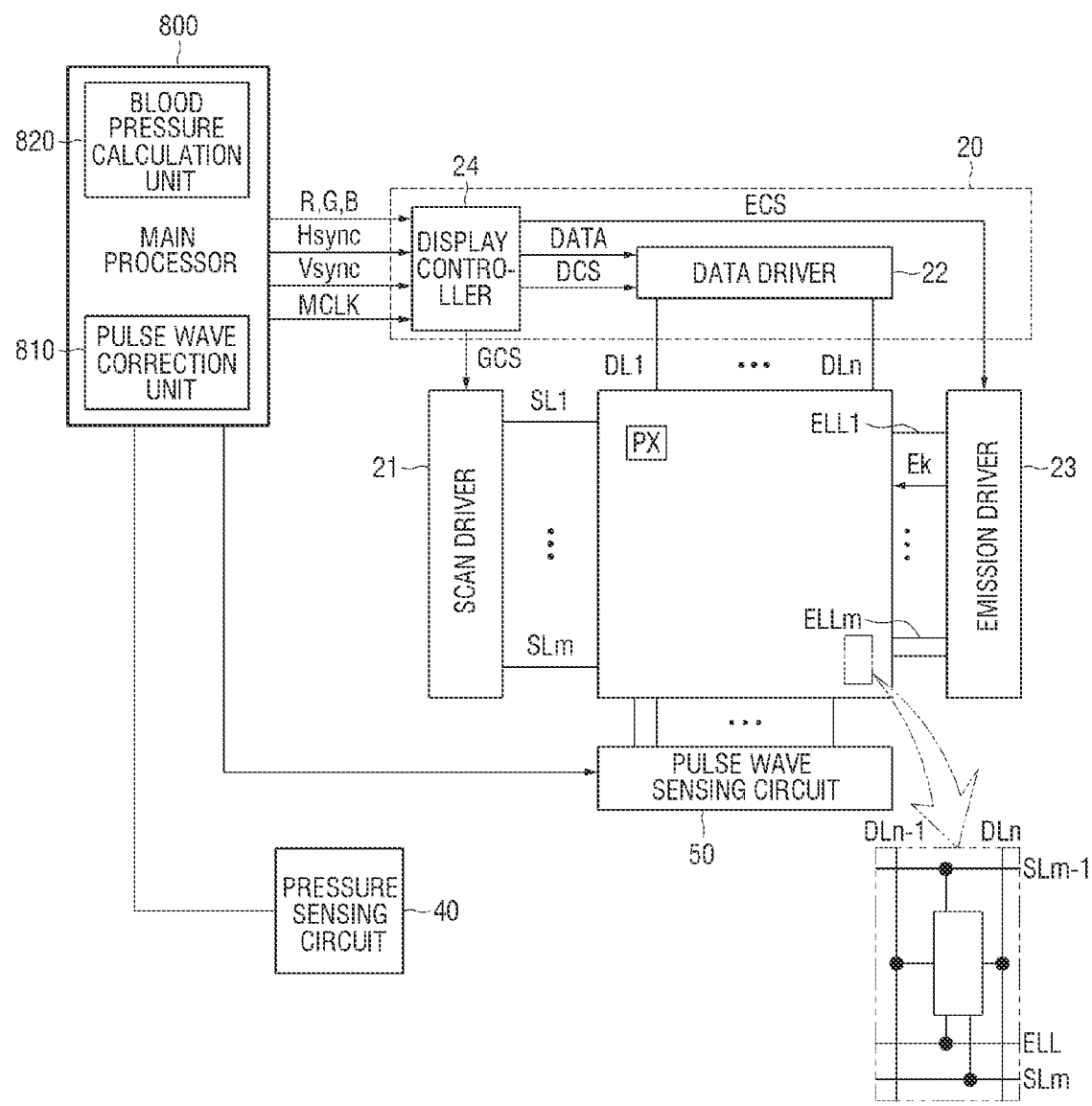
FIG. 3 is a block diagram illustrating the display device according to an embodiment.

FIG. 3 is a block diagram illustrating the display device according to an embodiment.

Referring to FIG. 3, the display device 1 includes the display panel 10 including the plurality of pixels PX, the display driver 20, a scan driver 21, an emission driver 23, the pulse wave sensing circuit 50, the pressure sensing circuit 40, and the main processor 800.

The main processor 800 includes a pulse wave correction unit (e.g., a pulse wave corrector) 810 and a blood pressure calculation unit (e.g., a blood pressure calculator) 820.

The pulse wave correction unit 810 may receive the optical signal from the pulse wave sensing circuit 50. In addition, the pulse wave correction unit 810 may receive the electrical signal from the pressure sensing circuit 40. The pulse wave correction unit 810 may generate a pulse wave signal (e.g., an initial pulse wave signal), in which noise components for the user are blocked or reduced based on the received signals. The pulse wave correction unit 810 may calculate a pulse wave signal PPG reflecting a blood change depending on a heartbeat according to the pulse wave signal (e.g., the initial pulse wave signal). The pulse wave correction unit 810 may output the pulse wave signal PPG to the blood pressure calculation unit 820. The pulse wave correction unit 810 will be described in more detail below with reference to FIG. 6.

The blood pressure calculation unit 820 may receive the pulse wave signal PPG from the pulse wave correction unit 810. The blood pressure calculation unit 820 may calculate a blood pressure of the user based on the pulse wave signal PPG.

The main processor 800 drives and controls the pulse wave sensing circuit 50, the pressure sensing circuit 40, and a display controller 24. The main processor 800 may output image information to the display controller 24. For example, the main processor 800 may output image information including the calculated pulse wave signal PPG, a blood pressure measurement value, and blood pressure information to the display controller 24.

The display controller 24 receives the image information supplied from the main processor 800. In addition, the display controller 24 may generate a scan control signal GCS for controlling an operation timing of the scan driver 21, an emission control signal ECS for controlling an operation timing of the emission driver 23, and a data control signal DCS for controlling an operation timing of a data driver 22. The display controller 24 may output image data DATA and the data control signal DCS to the data driver 22. The display controller 24 may output the scan control signal GCS to the scan driver 21, and the emission control signal ECS to the emission driver 23.

The display controller 24 may be electrically connected to the display panel 10 and/or the main processor 800 through lines, or may be connected to the display panel 10 and/or the main processor 800 through a communication network. In an embodiment, at least a portion of the display controller 24 may be directly attached onto the display panel 10 in the form of a driving chip.

The data driver 22 may receive the image data DATA and the data control signal DCS from the display controller 24. The data driver 22 may convert the image data DATA into analog data voltages according to the data control signal DCS. The data driver 22 may output the converted analog data voltages to data lines DL1 to DLn, where n is a natural number, in synchronization with scan signals.

The scan driver 21 may generate the scan signals according to the scan control signal GCS, and may sequentially output the scan signals to scan lines SL1 to SLm, where m is a natural number.

In some embodiments, the display device 1 may further include a driving voltage, a common voltage, and a source voltage line. The source voltage line may include a driving voltage line and a common voltage line. The driving voltage may be a high potential voltage for driving light emitting elements and photoelectric conversion elements, and the common voltage may be a low potential voltage for driving the light emitting elements and the photoelectric conversion elements. In other words, the driving voltage may have a higher potential than that of the common voltage.

A display control signal may include the scan control signal GCS, the data control signal DCS, and the emission control signal ECS. The display control signal may be output to the scan driver 21, the data driver 22, and the emission driver 23.

The emission driver 23 may generate emission signals Ek according to the emission control signal ECS, and may sequentially output the emission signals Ek to emission lines ELL1 to ELLm, where m is a natural number. While FIG. 3 shows that the emission driver 23 is separate from the scan driver 21, the present disclosure is not limited thereto, and in some embodiments, the emission driver 23 may be included in the scan driver 21.

The data driver 22 and the display controller 24 may be included in the display driver 20 for controlling an operation of the display panel 10. The data driver 22 and the display controller 24 may be formed as integrated circuits (ICs), and may be mounted on the display driver 20.

Each of the plurality of pixels PX may be connected to at least one of the scan lines SL1 to SLm, any one of the data lines DL1 to DLn, and at least one of the emission lines ELL1 to ELLm.

Each of the plurality of photo-sensors PS may be connected to any one of the scan lines SL1 to SLm, and any one of readout lines.

The plurality of scan lines SL1 to SLm may connect the scan driver 21 to the plurality of pixels PX and the plurality of photo-sensors PS. The plurality of scan lines SL1 to SLm may provide the scan signals output from the scan driver 21 to the plurality of pixels PX.

The plurality of data lines DL1 to DLn may connect the data driver 22 to the plurality of pixels PX. The plurality of data lines DL1 to DLn may provide data signals (e.g., the analog data voltages) output from the data driver 22 to the plurality of pixels PX.

The plurality of emission lines ELL1 to ELLm may connect the emission driver 23 to the plurality of pixels PX. The plurality of emission lines ELL1 to ELLm may provide the emission signals Ek output from the emission driver 23 to the plurality of pixels PX.

Figure 4:
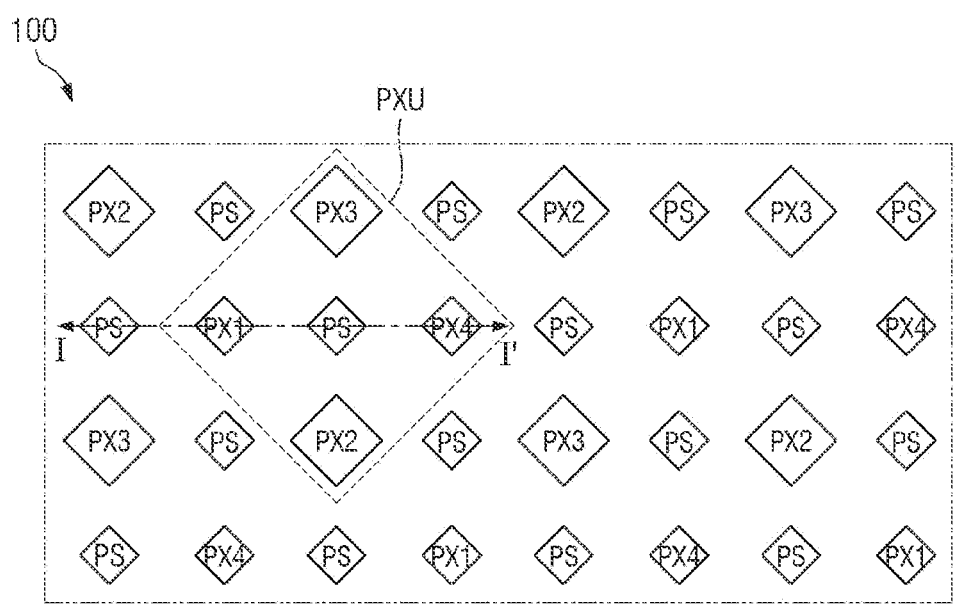
FIG. 4 is a plan layout view of pixels and photo-sensors of a display cell according to an embodiment.
Figure 4:
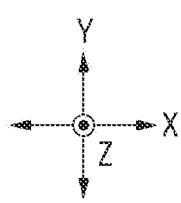

FIG. 4 is a plan layout view of pixels and photo-sensors of a display cell according to an embodiment.

Referring to FIG. 4, a plurality of pixels PX and a plurality of photo-sensors PS may be repeatedly disposed in a display cell 100.

The plurality of pixels PX may include first sub-pixels PX1, second sub-pixels PX2, third sub-pixels PX3, and fourth sub-pixels PX4. For example, the second sub-pixels PX2 may emit light of a red wavelength, the first sub-pixels PX1 and the fourth sub-pixels PX4 may emit light of a green wavelength, and the third sub-pixels PX3 may emit light of a blue wavelength.

However, when a blood pressure is measured as described in more detail below, the first sub-pixels PX1 may emit green light, and the second sub-pixels PX2 may emit light of an infrared region, but the present disclosure is not limited thereto. As another example, the first sub-pixels PX1 may emit blue or green light, and the second sub-pixels PX2 may emit red light or light of an infrared region.

The plurality of pixels PX may include a plurality of emission areas for emitting light, respectively. The plurality of photo-sensors PS may include a plurality of light sensing areas for sensing light incident thereon.

The first sub-pixels PX1, the second sub-pixels PX2, the third sub-pixels PX3, the fourth sub-pixels PX4, and the plurality of photo-sensors PS may be alternately arranged along a first direction X and a second direction Y. In an embodiment, the second sub-pixels PX2 and the third sub-pixels PX3 may be alternately arranged along the first direction X, while forming a first row extending in the first direction X, and the first sub-pixels PX1 and the fourth sub-pixels PX4 may be repeatedly arranged along the first direction X in a second row adjacent to the first row. The pixels PX belonging to the first row may be disposed to be misaligned with the pixels PX belonging to the second row in the second direction Y. Arrangements of the first row and the second row may be repeated up to an m-th row, where m is a natural number.

The photo-sensors PS may be disposed between the second sub-pixels PX2 and the third sub-pixels PX3 forming the first row, and may be spaced apart from each other. The second sub-pixels PX2, the photo-sensors PS, and the third sub-pixels PX3 may be alternately arranged along the first direction X. The photo-sensors PS may be disposed between the first sub-pixels PX1 and the fourth sub-pixels PX4 forming the second row, and may be spaced apart from each other. The first sub-pixels PX1, the photo-sensors PS, and the fourth sub-pixels PX4 may be alternately arranged along the first direction X. The number of photo-sensors PS in the first row may be the same or substantially the same as the number of photo-sensors PS in the second row. Arrangements of the first row and the second row may be repeated up to the m-th row.

As another example, the photo-sensors PS may be disposed between the first sub-pixels PX1 and the fourth sub-pixels PX4 forming the second row, and may not be disposed between the second sub-pixels PX2 and the third sub-pixels PX3 forming the first row. In other words, the photo-sensors PS may not be disposed in the first row.

Sizes of emission areas of the pixels PX may be different from one another. Sizes of the emission areas of the first sub-pixels PX1 and the fourth sub-pixels PX4 may be smaller than those of the emission areas of the second sub-pixels PX2 and/or the third sub-pixels PX3. While FIG. 4 illustrates that the pixels PX have a rhombic shape, the present disclosure is not limited thereto, and the pixels PX have may have any suitable shape, such as a rectangular shape, an octagonal shape, other suitable polygonal shapes, a circular shape, or the like.

One pixel unit PXU may include one first sub-pixel PX1, one second sub-pixel PX2, one third sub-pixel PX3, and one fourth sub-pixel PX4. The pixel unit PXU refers to a group of color pixels capable of expressing a gradation (e.g., grayscale values).

Figure 5:
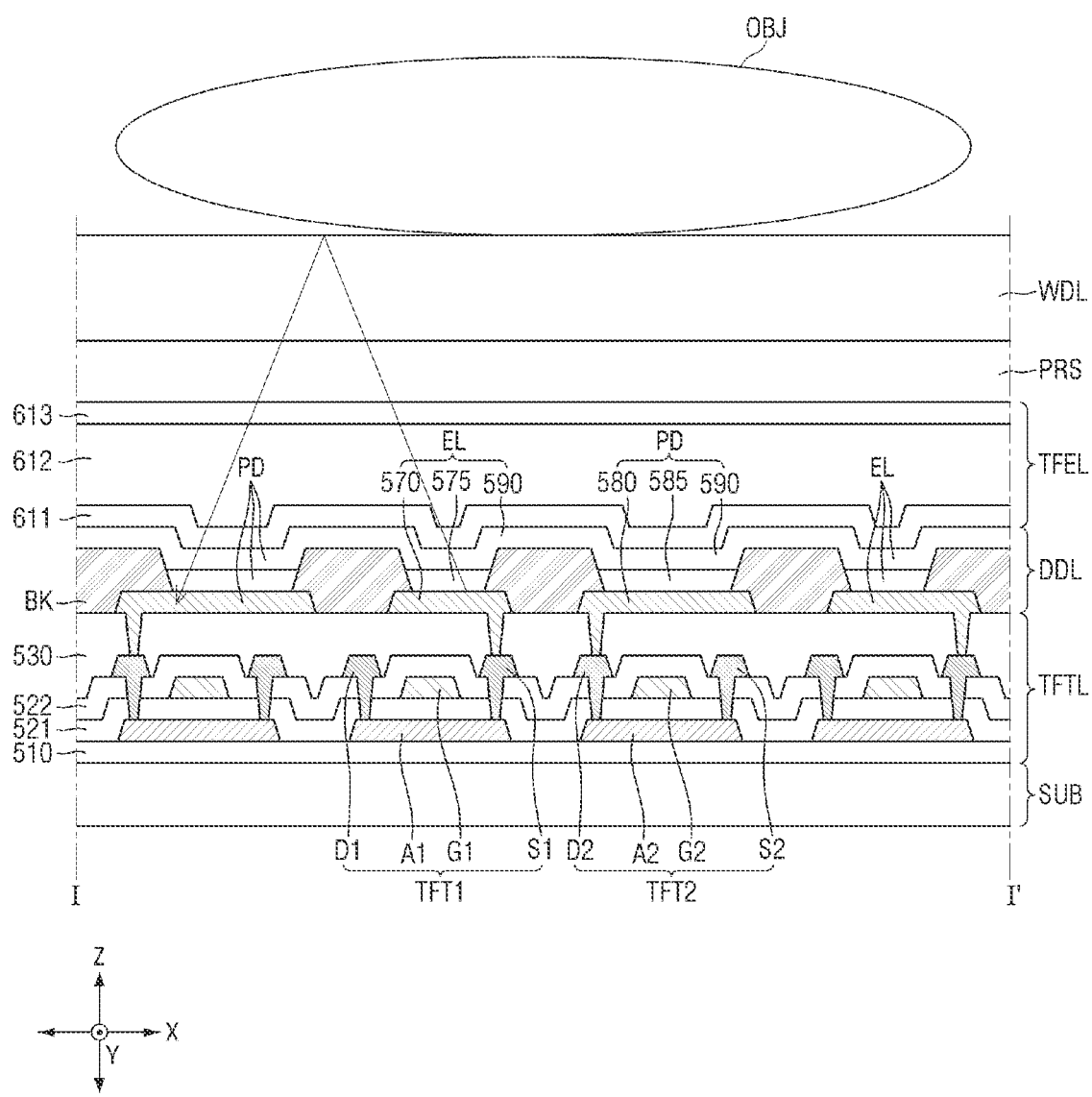
FIG. 5 is a cross-sectional view taken along the line I-I' of FIG. 4.

FIG. 5 is a cross-sectional view taken along the line I-I' of FIG. 4.

Referring to FIG. 5, a buffer layer 510 is disposed on a substrate SUB. The buffer layer 510 may include silicon nitride, silicon oxide, silicon oxynitride, or the like.

A first thin film transistor TFT1 and a second thin film transistor TFT2 may be disposed on the buffer layer 510.

The plurality of thin film transistors TFT1 and TFT2 may include semiconductor layers A1 and A2, a gate insulating layer 521 disposed on portions of the semiconductor layers A1 and A2, gate electrodes G1 and G2 disposed on the gate insulating layer 521, an interlayer insulating film 522 covering each of the semiconductor layers A1 and A2 and each of the gate electrodes G1 and G2, and source electrodes S1 and S2 and drain electrodes D1 and D2 disposed on the interlayer insulating film 522.

The semiconductor layers A1 and A2 may form channels of the first thin film transistor TFT1 and the second thin film transistor TFT2, respectively. The semiconductor layers A1 and A2 may include polycrystalline silicon. In another embodiment, the semiconductor layers A1 and A2 may include single crystal silicon, low-temperature polycrystalline silicon, amorphous silicon, or an oxide semiconductor. The oxide semiconductor may include, for example, a binary compound ($AB_x$), a ternary compound ($AB_xC_y$), or a quaternary compound ($AB_xC_yD_z$) containing indium, zinc, gallium, tin, titanium, aluminum, hafnium (Hf), zirconium (Zr), magnesium (Mg), and/or the like. The semiconductor layers A1 and A2 may include channel regions, and source regions and drain regions doped with impurities.

The gate insulating layer 521 is disposed on the semiconductor layers A1 and A2. The gate insulating layer 521 electrically insulates a first gate electrode G1 and a first semiconductor layer A1 from each other, and electrically insulates a second gate electrode G2 and a second semiconductor layer A2 from each other. The gate insulating layer 521 may include (e.g., may be made of) an insulating material, for example, such as silicon oxide ($SiO_x$), silicon nitride ($SiN_x$), or a metal oxide.

The first gate electrode G1 of the first thin film transistor TFT1 and the second gate electrode G2 of the second thin film transistor TFT2 are disposed on the gate insulating layer 521. The gate electrodes G1 and G2 may be formed above the channel regions of the semiconductor layers A1 and A2, or in other words, on positions of the gate insulating layer 521 overlapping with the channel regions, respectively.

The interlayer insulating film 522 may be disposed on the gate electrodes G1 and G2. The interlayer insulating film 522 may include an inorganic insulating material, such as silicon oxide ($SiO_x$), silicon nitride ($SiN_x$), silicon oxynitride, hafnium oxide, or aluminum oxide. In addition, in some embodiments, the interlayer insulating film 522 may include a plurality of insulating films, and may further include a conductive layer disposed between the plurality of insulating films to form a capacitor second electrode.

The source electrodes S1 and S2 and the drain electrodes D1 and D2 are disposed on the interlayer insulating film 522. A first source electrode S1 of the first thin film transistor TFT1 may be electrically connected to the drain region (or the source region) of the first semiconductor layer A1 through a contact hole penetrating through the interlayer insulating film 522 and the gate insulating layer 521. A second source electrode S2 of the second thin film transistor TFT2 may be electrically connected to the drain region (or the source region) of the second semiconductor layer A2 through a contact hole penetrating through the interlayer insulating film 522 and the gate insulating layer 521. Each of the source electrodes S1 and S2 and the drain electrodes D1 and D2 may include one or more suitable metals selected from the group consisting of aluminum (Al), molybdenum (Mo), platinum (Pt), palladium (Pd), silver (Ag), magnesium (Mg), gold (Au), nickel (Ni), neodymium (Nd), iridium (Ir), chromium (Cr), calcium (Ca), titanium (Ti), tantalum (Ta), tungsten (W), and copper (Cu).

A planarization layer 530 may be formed on the interlayer insulating film 522, so as to cover each of the source electrodes S1 and S2 and the drain electrodes D1 and D2. The planarization layer 530 may include (e.g., may be made of) an organic insulating material or the like. The planarization layer 530 may have a flat or substantially flat surface, and includes contact holes exposing the source electrodes S1 and S2 and/or the drain electrodes D1 and D2.

A light emitting element layer DDL may be disposed on the planarization layer 530. The light emitting element layer DDL may include light emitting elements EL, photoelectric conversion elements PD, and a bank layer BK. The light emitting element EL may include a pixel electrode 570, an emission layer 575, and a common electrode 590. The photoelectric conversion element PD may include a first electrode 580, a photoelectric conversion layer 585, and the common electrode 590.

The pixel electrode 570 of the light emitting element EL may be disposed on the planarization layer 530. A plurality of pixel electrodes 570 may be provided on the planarization layer 530, one for each pixel PX. The pixel electrode 570 may be connected to the first source electrode S1 or the first drain electrode D1 of the first thin film transistor TFT1 through a contact hole penetrating through the planarization layer 530.

The pixel electrode 570 of the light emitting element EL may have a single-layer structure of molybdenum (Mo), titanium (Ti), copper (Cu), or aluminum (Al), or may have a stacked film structure, for example, such as a multilayered structure of ITO/Mg, ITO/MgF, ITO/Ag, or ITO/Ag/ITO, including indium-tin-oxide (ITO), indium-zinc-oxide (IZO), zinc oxide (ZnO), or indium oxide ($In_2O_3$), and silver (Ag), magnesium (Mg), aluminum (Al), platinum (Pt), lead (Pb), gold (Au), or nickel (Ni), but is not limited thereto.

The first electrode 580 of the photoelectric conversion element PD may also be disposed on the planarization layer 530. A plurality of first electrodes 580 may be provided on the planarization layer 530, one for each photo-sensor PS. The first electrode 580 may be connected to the second source electrode S2 or the second drain electrode D2 of the second thin film transistor TFT2 through a contact hole penetrating through the planarization layer 530.

The first electrode 580 of the photoelectric conversion element PD may have a single-layer structure of molybdenum (Mo), titanium (Ti), copper (Cu), or aluminum (Al), or may have a multilayered structure of ITO/Mg, ITO/MgF, ITO/Ag, or ITO/Ag/ITO, but is not limited thereto.

The bank layer BK may be disposed on the pixel electrode 570 and the first electrode 580. The bank layer BK may include openings formed in areas overlapping with the pixel electrodes 570, and exposing the pixel electrodes 570. Areas in which the exposed pixel electrodes 570 and the emission layers 575 overlap with each other may be defined as emission areas for emitting different color light according to the corresponding pixels PX, which include the first sub-pixels PX1, the second sub-pixels PX2, the third sub-pixels PX3, and the fourth sub-pixels PX4 as described above.

In addition, the bank layer BK may include openings formed in areas overlapping with the first electrodes 580, and exposing the first electrodes 580. The openings exposing the first electrodes 580 may provide spaces in which the photoelectric conversion layers 585 of the photo-sensors PS are formed, respectively, and areas in which the exposed first electrodes 580 and the photoelectric conversion layers 585 overlap with each other may be defined as light sensing parts.

The bank layer BK may include an organic insulating material, such as a polyacrylates resin, an epoxy resin, a phenolic resin, a polyamides resin, a polyimides resin, an unsaturated polyesters resin, a polyphenyleneethers resin, a polyphenylenesulfides resin, or benzocyclobutene (BCB). As another example, the bank layer BK may also include an inorganic material, such as silicon nitride.

The emission layers 575 may be disposed on the pixel electrodes 570 of the light emitting elements EL exposed by the openings of the bank layer BK. The emission layer 575 may include a high molecular material or a low molecular material, and may emit red, green, or blue light according to the color of light emitted by the corresponding pixel PX. The light emitted from the emission layer 575 may contribute to an image display, or may function as a light source incident on the photo-sensor PS. For example, light sources of a green wavelength emitted from the emission areas of the first sub-pixel PX1 and the fourth sub-pixel PX4 may function as light sources incident on the light sensing areas of the photo-sensors PS.

When the emission layer 575 is formed of an organic material, a hole injecting layer (HIL) and/or a hole transporting layer (HTL) may be disposed at a lower portion of each of the emission layers 575, and an electron injecting layer (EIL) and/or an electron transporting layer (ETL) may be stacked at an upper portion of each of the emission layers 175. Each of the HIL, HTL, EIL, and ETL layers may be a single layer or multiple layers including (e.g., made of) an organic material.

The photoelectric conversion layers 585 may be disposed on the first electrodes 580 of the photoelectric conversion elements PD exposed by the openings of the bank layer BK. Areas in which the exposed first electrodes 580 and the photoelectric conversion layers 585 overlap with each other may be defined as the light sensing areas of the photo-sensors PS, respectively. The photoelectric conversion layer 585 may generate photocharges in proportion to incident light. The incident light may be light emitted from the emission layer 575, and then reflected to enter the photoelectric conversion layer 585, or may be light provided from the outside regardless of the light emitted by the emission layer 575. Charges generated and accumulated in the photoelectric conversion layer 585 may be converted into electrical signals used for sensing.

The photoelectric conversion layer 585 may include an electron donating material, and an electron accepting material. The electron donating material may generate donor ions in response to light, and the electron accepting material may generate acceptor ions in response to light. When the photoelectric conversion layer 585 is formed of an organic material, the electron donating material may include a suitable compound, such as subphthalocyanine (SubPc) or dibutylphosphate (DBP), but is not limited thereto. The electron accepting material may include a suitable compound, such as fullerene, a fullerene derivative, or perylene diimide, but is not limited thereto.

As another example, when the photoelectric conversion layer 585 is formed of an inorganic material, the photoelectric conversion element PD may be a pn-type or pin-type phototransistor. For example, the photoelectric conversion layer 585 may have a structure in which an N-type semiconductor layer, an I-type semiconductor layer, and a P-type semiconductor layer are sequentially stacked on one another.

When the photoelectric conversion layer 585 is formed of the organic material, a hole injecting layer (HIL) and/or a hole transporting layer (HTL) may be disposed at a lower portion of each of the photoelectric conversion layers 585, and an electron injecting layer (EIL) and/or an electron transporting layer (ETL) may be stacked at an upper portion of each of the photoelectric conversion layers 585. Each of the HIL, HTL, EIL, and ETL layers may be a single layer or multiple layers including (e.g., made of) an organic material.

The common electrode 590 may be disposed on the emission layers 575, the photoelectric conversion layers 585, and the bank layer BK. The common electrode 590 may be disposed throughout the plurality of pixels PX and the plurality of photo-sensors PS in a form to cover the emission layers 575, the photoelectric conversion layers 585, and the bank layer BK. The common electrode 590 may include a material layer having a small work function, for example, such as Li, Ca, LiF/Ca, LiF/Al, Al, Mg, Ag, Pt, Pd, Ni, Au, Nd, Ir, Cr, BaF, Ba, or suitable compounds or mixtures thereof (e.g., a mixture of Ag and Mg, or the like). As another example, the common electrode 590 may include a transparent metal oxide, for example, such as indium-tin-oxide (ITO), indium-zinc-oxide (IZO), or zinc oxide (ZnO).

The common electrode 590 may be disposed in common on the emission layer 575 and the photoelectric conversion layer 585, but is not limited thereto. In this case, a cathode electrode of the light emitting element EL and a sensing cathode electrode of the photoelectric conversion element PD may be electrically connected to each other. For example, a common voltage line connected to the cathode electrode of the light emitting element EL may also be connected to the sensing cathode electrode of the photoelectric conversion element PD.

An encapsulation layer TFEL may be disposed on the light emitting element layer DDL. The encapsulation layer TFEL may include at least one inorganic film to prevent or substantially prevent oxygen and/or moisture from penetrating into the emission layer 575 and the photoelectric conversion layer 585. In addition, the encapsulation layer TFEL may include at least one organic film to protect the emission layer 575 and the photoelectric conversion layer 585 from foreign materials, such as dust. For example, the encapsulation layer TFEL may be formed in a structure in which a first inorganic film 611, an organic film 612, and a second inorganic film 613 are sequentially stacked on one another. Each of the first inorganic film 611 and the second inorganic film 613 may be formed as multiple films, in which one or more inorganic films of a silicon nitride layer, a silicon oxynitride layer, a silicon oxide layer, a titanium oxide layer, and/or an aluminum oxide layer are alternately stacked on one another. The organic film 612 may include (e.g., may be made of) an acrylic resin, an epoxy resin, a phenolic resin, a polyamide resin, a polyimide resin, or the like.

A pressure sensing layer PRS may be disposed on the encapsulation layer TFEL. The pressure sensing layer PRS may be provided in the form of a panel or a film, and may be attached onto the encapsulation layer TFEL through a bonding layer, for example, such as a pressure sensitive adhesive (PSA). The pressure sensing layer PRS is positioned on a light emission path of the light emitting element layer DDL, and thus, may be transparent.

The pressure sensing layer PRS serves to sense a pressure applied to the display device 1. When the user or the like contacts (e.g., touches) an upper surface of the display device 1, a pressure applying force of a touch input may be sensed by the pressure sensing layer PRS. A pressure sensing electrode of the pressure sensing layer PRS may be directly formed on a touch layer. In this case, the pressure sensing layer PRS may be incorporated in the display panel 10, together with the light emitting element layer DDL and the touch layer.

A window WDL may be disposed on the pressure sensing layer PRS. The window WDL may be disposed on the display device 1 to protect components of the display device 1, after a cutting process and a module process of the display cell 100 are performed. The window WDL may include (e.g., may be made of) glass or plastic.

FIG. 5 is a cross-sectional view illustrating a state in which a finger of a user OBJ is in contact with the window WDL of the display device 1. When the finger or the like of the user OBJ is in contact with an upper surface of the window WDL, light output from the emission areas of the pixels PX may be reflected from the finger or the like of the user OBJ. In this case, blood flow rates according to pressure in a blood vessel of the finger or the like of the user OBJ may be different from each other. Accordingly, the blood flow rate of the blood vessel of the finger or the like of the user OBJ may be derived based on a difference in an amount of the reflected light, or in other words, the light incident on the photo-sensors PS. A blood pressure of the user OBJ may be measured through the photo-sensors PS and the pressure sensing layer PRS.

Figure 6:
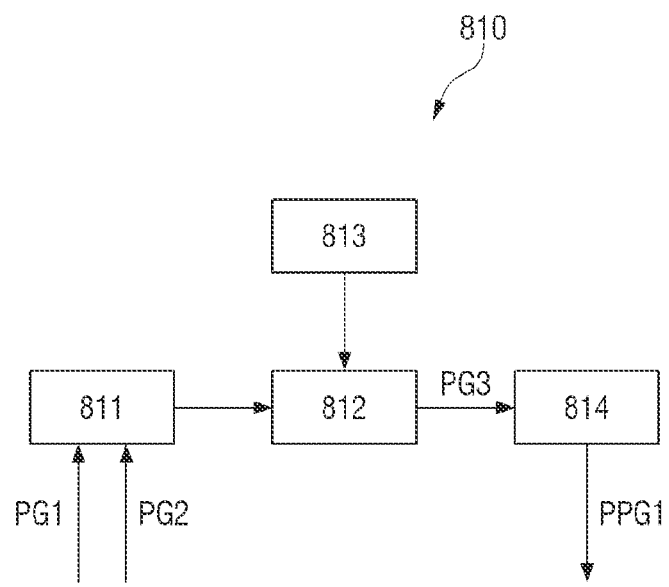
FIG. 6 is a block diagram illustrating a pulse wave correction unit according to an embodiment.

FIG. 6 is a block diagram illustrating a pulse wave correction unit according to an embodiment.

The pulse wave correction unit 810 includes a calculator 811, a corrector 812, a memory 813, and a pulse wave signal generator 814.

The calculator 811 may receive the optical signal from the pulse wave sensing circuit 50. In more detail, the calculator 811 may receive a first pulse wave signal PG1 by light emitted from the first sub-pixels. In addition, the calculator 811 may receive a second pulse wave signal PG2 by light emitted from the second sub-pixels. The calculator 811 may calculate maximum values of the first pulse wave signal PG1 and the second pulse wave signal PG2. The calculator 811 may output information of the first pulse wave signal PG1 and the second pulse wave signal PG2 to the corrector 812.

The corrector 812 may receive the information of the first pulse wave signal PG1 and the second pulse wave signal PG2 from the calculator 811. The corrector 812 may remove or reduce noise components for the user from a pulse signal based on the received information. For example, information based on an amount of light reflected from the user's capillaries, skin, tissues, and/or the like may be removed or reduced from the second pulse wave signal PG2. The corrector 812 may generate a third pulse wave signal PG3, in which noise from the user is removed or reduced. The corrector 812 may output the third pulse wave signal PG3 to the pulse wave signal generator 814. A method of removing or reducing the noise for the user by the corrector 812 will be described in more detail below with reference to FIGS. 7 through 13.

The memory 813 may store information for removing noise for the user by the corrector 812. The memory 813 may store data used by the corrector 812 to remove or reduce the noise based on the amount of light reflected from the user's capillaries, skin, tissues, and/or the like, from the second pulse wave signal PG2. The memory 813 may output the stored data to the corrector 812.

The pulse wave signal generator 814 may receive the third pulse wave signal PG3 from the corrector 812. In addition, the pulse wave signal generator 814 may receive the electrical signal from the pressure sensing circuit 40. The pulse wave signal generator 814 may calculate the pulse wave signal PPG (e.g., PPG1 shown in FIG. 6) for reflecting the blood change depending on the heartbeat according to the pulse wave signal (e.g., the third pulse wave signal PG3). The pulse wave signal generator 814 may output the pulse wave signal PPG (e.g., PPG1 shown in FIG. 6) to the blood pressure calculator 811.

Figure 7:
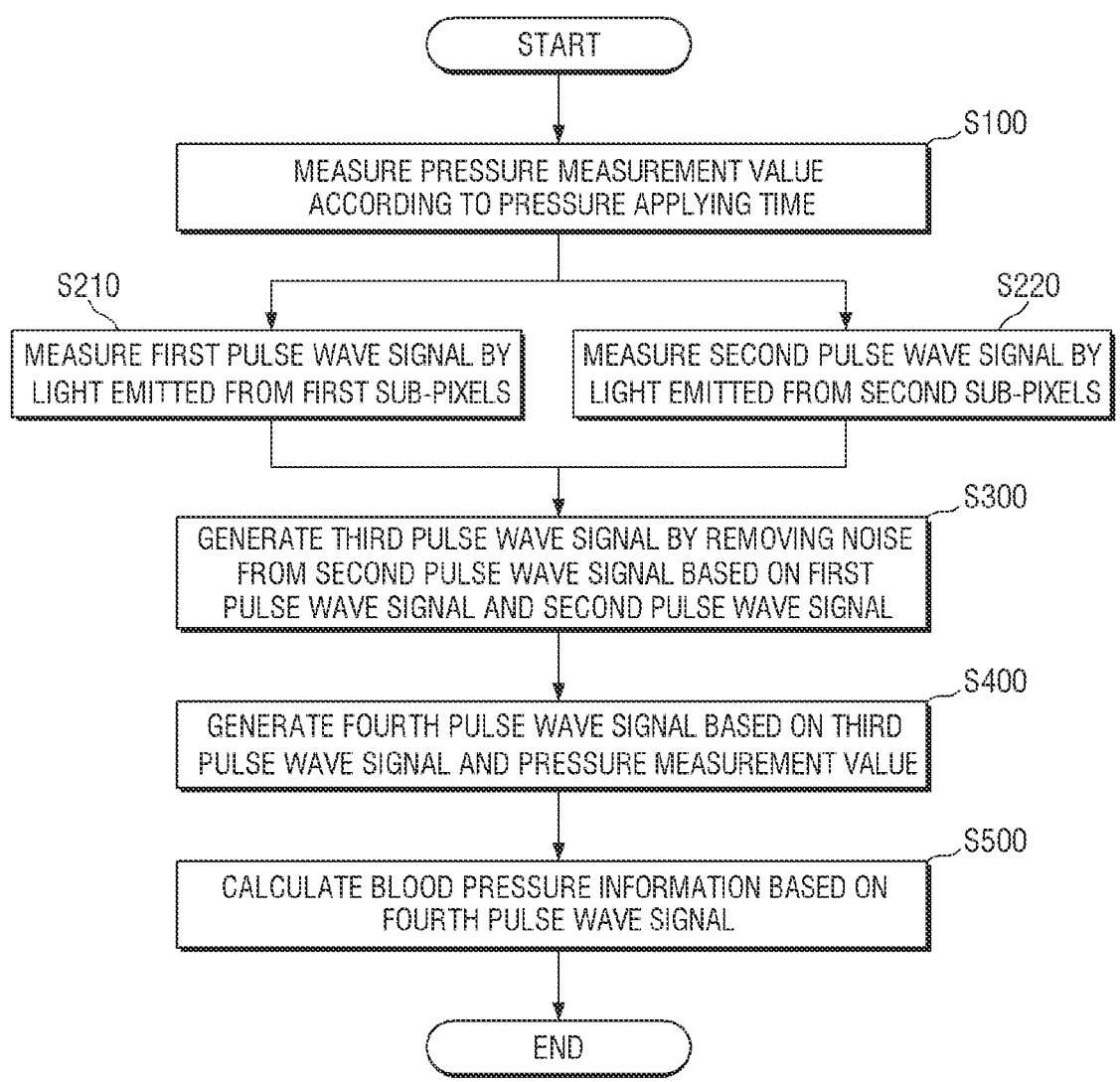
FIG. 7 is a flowchart illustrating a blood pressure measurement method using the display device according to an embodiment.
Figure 8:
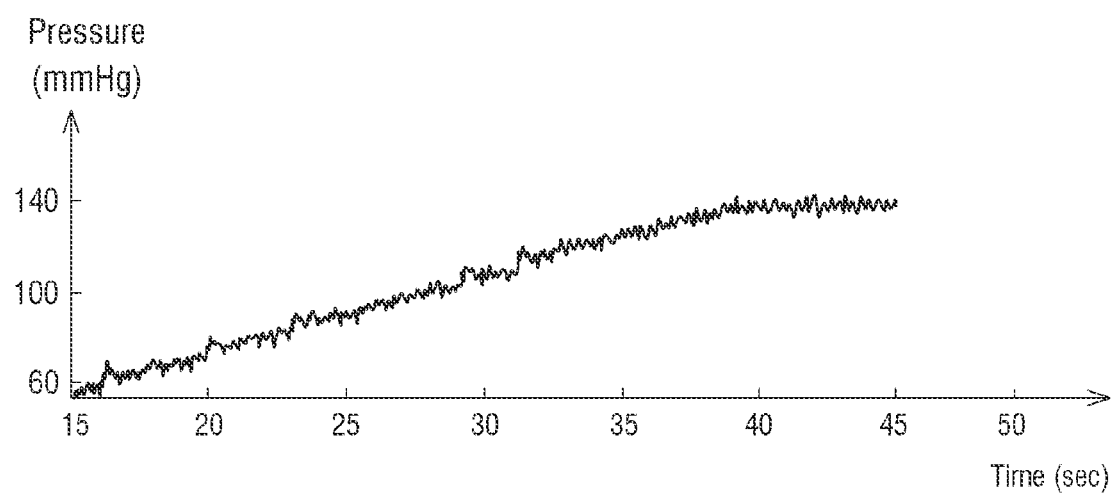
FIG. 8 is a graph illustrating pressure measurement values according to a pressure applying time.

FIG. 7 is a flowchart illustrating a blood pressure measurement method using the display device according to an embodiment. FIG. 8 is a graph illustrating pressure measurement values according to a pressure applying time.

A blood pressure measurement method using the display device 1 will be described in more detail with reference to FIGS. 7 and 8.

First, the pressure sensing circuit 40 measures a pressure measurement value according to a pressure applying time (S100).

Referring further to FIG. 8, the user may apply pressure to a position where the pressure sensor is disposed, and the pressure sensor may measure a pressure measurement value of the pressure applied by the user. For example, in a process in which the user brings his/her finger into contact with the display device 1, the pressure measurement value measured by the pressure sensor may gradually increase over time to reach a maximum value. When the pressure measurement value (e.g., a contact pressure) increases, a blood vessel may be constricted, such that a blood flow rate may be decreased or become 0.

Next, the pulse wave sensing circuit 50 measures a first pulse wave signal PG1 generated by light emitted from the first sub-pixels PX1 (S210), and measures a second pulse wave signal PG2 generated by light emitted from the second sub-pixels PX2 (S220).

In order to calculate the blood pressure information, pulse information according to time is used together with the pressure data. During systole of the heart, blood ejected from the left ventricle of the heart moves to peripheral tissues, such that a blood volume in the arterial side increases. In addition, during the systole of the heart, red blood cells carry more oxyhemoglobin to the peripheral tissues. During diastole of the heart, there is partial suction of blood from the peripheral tissues toward the heart. In this case, when the artery is irradiated with light emitted from a display pixel, the irradiated light may be absorbed by the peripheral tissue. Absorbance is dependent on a hematocrit and a blood volume. The absorbance may have a maximum value during the systole of the heart, and a minimum value during the diastole of the heart. Because the absorbance is in inverse proportion to an amount of light incident on a photo-sensor PS, absorbance at a corresponding point in time may be estimated through light reception data of the amount of light incident on the photo-sensor PS.

The amount of light incident on the photo-sensor PS may include data according to a heartbeat, as well as noise for the user. In more detail, the data according to the heartbeat is generated by receiving light reflected from the artery inside the skin tissue by the photo-sensor PS. The noise for the user is generated by receiving light reflected from the capillaries, the tissues, the skin, and the like by the photo-sensor PS. Accordingly, the pulse wave signal generated by the pulse wave sensing circuit 50 may include the pulse wave signal according to the heartbeat, as well as a pulse wave signal according to the noise for the user. Accordingly, accurate blood pressure information may be calculated by measuring the pulse wave signal regarding the noise for the user using a wavelength of the light emitted from the first sub-pixels PX1, which may be greater than a wavelength of the light emitted from the second sub-pixels PX2.

Therefore, in order to remove or reduce the noise for the user, the first sub-pixels PX1 may emit light of a relatively greater wavelength and the second sub-pixels PX2 may emit light of a relatively smaller wavelength. In addition, the pulse wave sensing circuit 50 may generate the first pulse wave signal PG1 generated according to the light emitted from the first sub-pixels PX1, and the second pulse wave signal PG2 generated according to the light emitted from the second sub-pixels PX2. Hereinafter, an emission area PPA (e.g., see FIG. 9) and a photo-sensor area PPB (e.g., see FIG. 12) of the display device for calculating the first pulse wave signal PG1 and the second pulse wave signal PG2 will be described in more detail.

Figure 9:
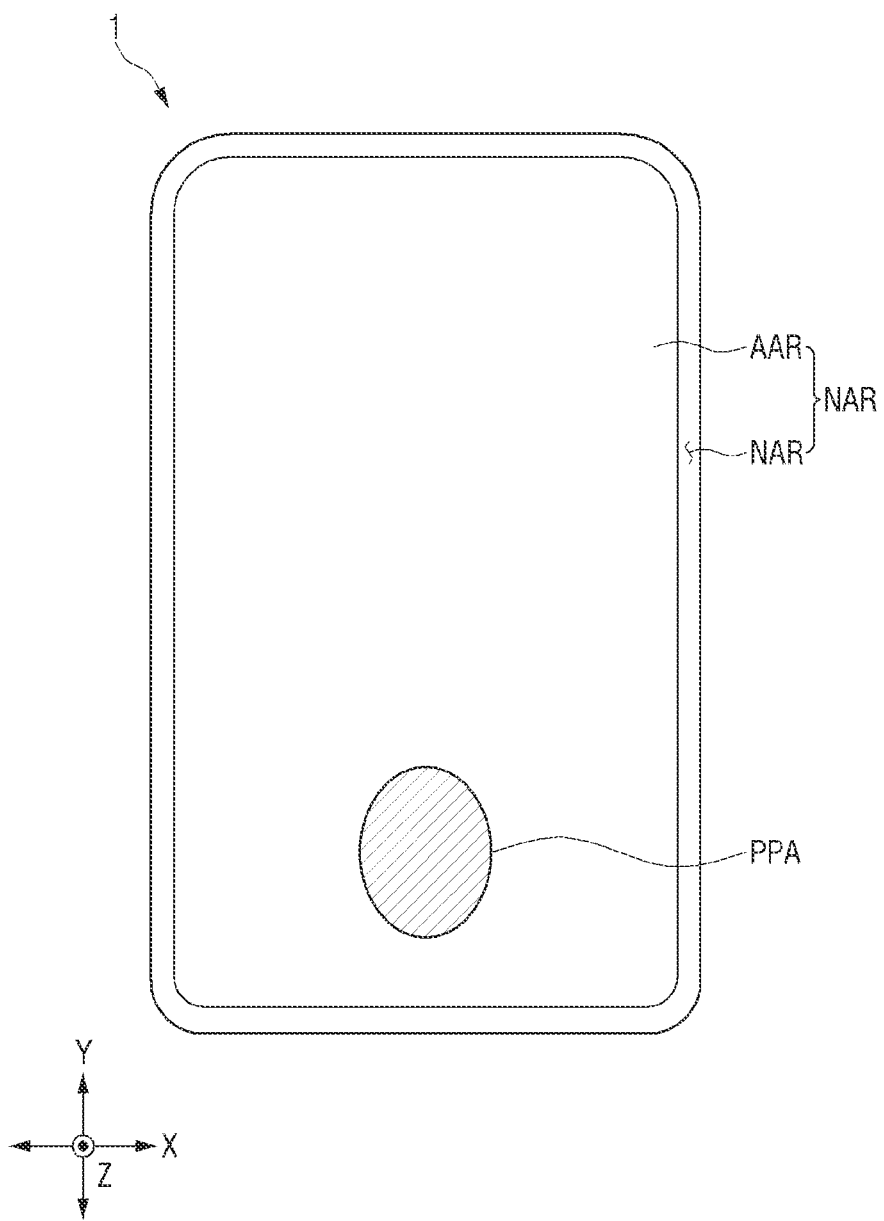
FIG. 9 is a plan view illustrating the blood pressure measurement method using the display device according to an embodiment.
Figure 10:
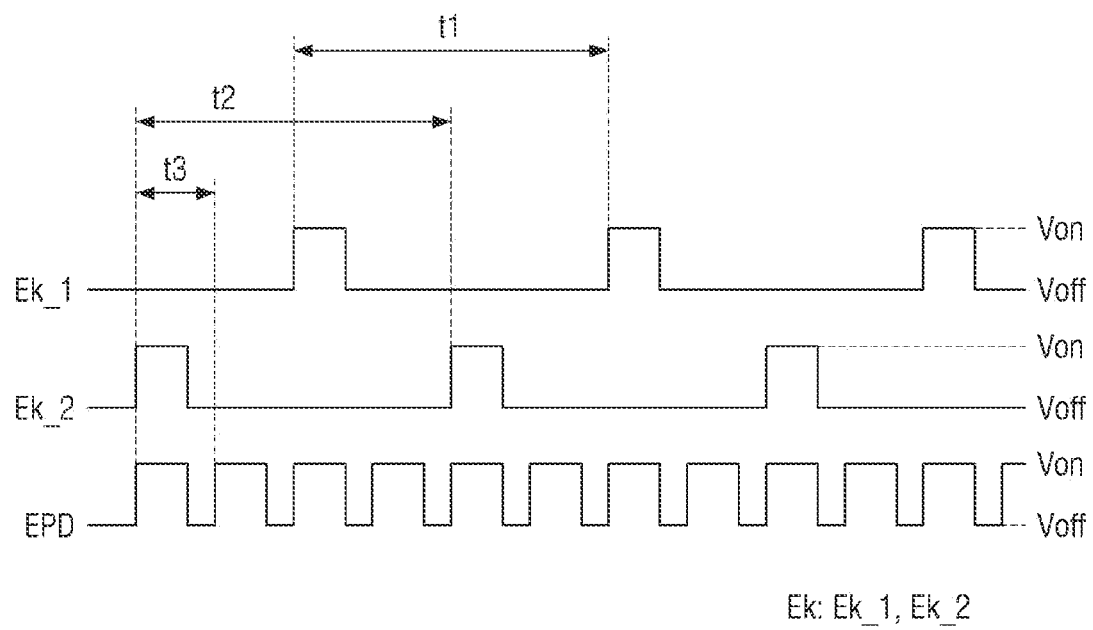
FIG. 10 is a waveform diagram illustrating emission signals of pixels and light sensing signals of photo-sensors of FIG. 9.

FIG. 9 is a plan view illustrating the blood pressure measurement method using the display device according to an embodiment. FIG. 10 is a waveform diagram illustrating emission signals of pixels and light sensing signals of photo-sensors of FIG. 9.

Referring further to FIGS. 9 and 10, the emission area PPA is disposed at (e.g., in or on) a partial area of the display area (e.g., of the active area AAR). In the present embodiment, the emission area PPA has a circular or elliptical shape. The emission area PPA includes one or more first sub-pixels PX1 and one or more second sub-pixels PX2. The emission area PPA may also include one or more third sub-pixels PX3, together with the first sub-pixels PX1 and the second sub-pixels PX2. However, the present disclosure is not limited thereto, and the emission area may include at least the first sub-pixels PX1 and the second sub-pixels PX2, or may include various suitable pixels.

As shown in FIG. 10, a first emission signal Ek_1 is a signal for controlling the turn-on and turn-off of the first sub-pixels PX1. A second emission signal Ek_2 is a signal for controlling the turn-on and turn-off of the second sub-pixels PX2. The first emission signal Ek_1 is a signal for controlling emission of the first sub-pixels PX1, and the second emission signal Ek_2 is a signal for controlling emission of the second sub-pixels PX2. A light sensing signal EPD is a signal for controlling the light sensing of the photo-sensors PS.

When a blood pressure is measured, the first light emitting signal Ek_1 and the second light emitting signal Ek_2 may alternately have a turn on level (e.g., may be alternately turned on). In more detail, one frame t1 of the first light emission signal Ek_1 and one frame t2 of the second light emission signal Ek_2 may be the same or substantially the same (e.g., may have the same or substantially the same length) as each other. In addition, one frame t3 of the light sensing signal EPD may be smaller (e.g., may be shorter) than the one frame t1 of the first emission signal Ek_1 and the one frame t2 of the second emission signal Ek_2. Accordingly, the first sub-pixels PX1 that are turned on according to the first emission signal Ek_1 and the second sub-pixels PX2 that are turned on according to the second emission signal Ek_2 may alternately emit light. For example, the first light emission signal Ek_1 and the second light emission signal Ek_2 may be turned on at a frequency of 60 Hz. However, the present disclosure is not limited thereto, and the first light emission signal Ek_1 and the second light emission signal Ek_2 may be turned on at a frequency of 120 Hz or higher.

As in the examples of the embodiments shown in FIGS. 9 and 10, the emission area PPA alternately emits light of different wavelengths, and thus, the photo-sensors PS may receive reflected light according to the light emitted from the first sub-pixels PX1 and the second sub-pixels PX2.

Figure 11:
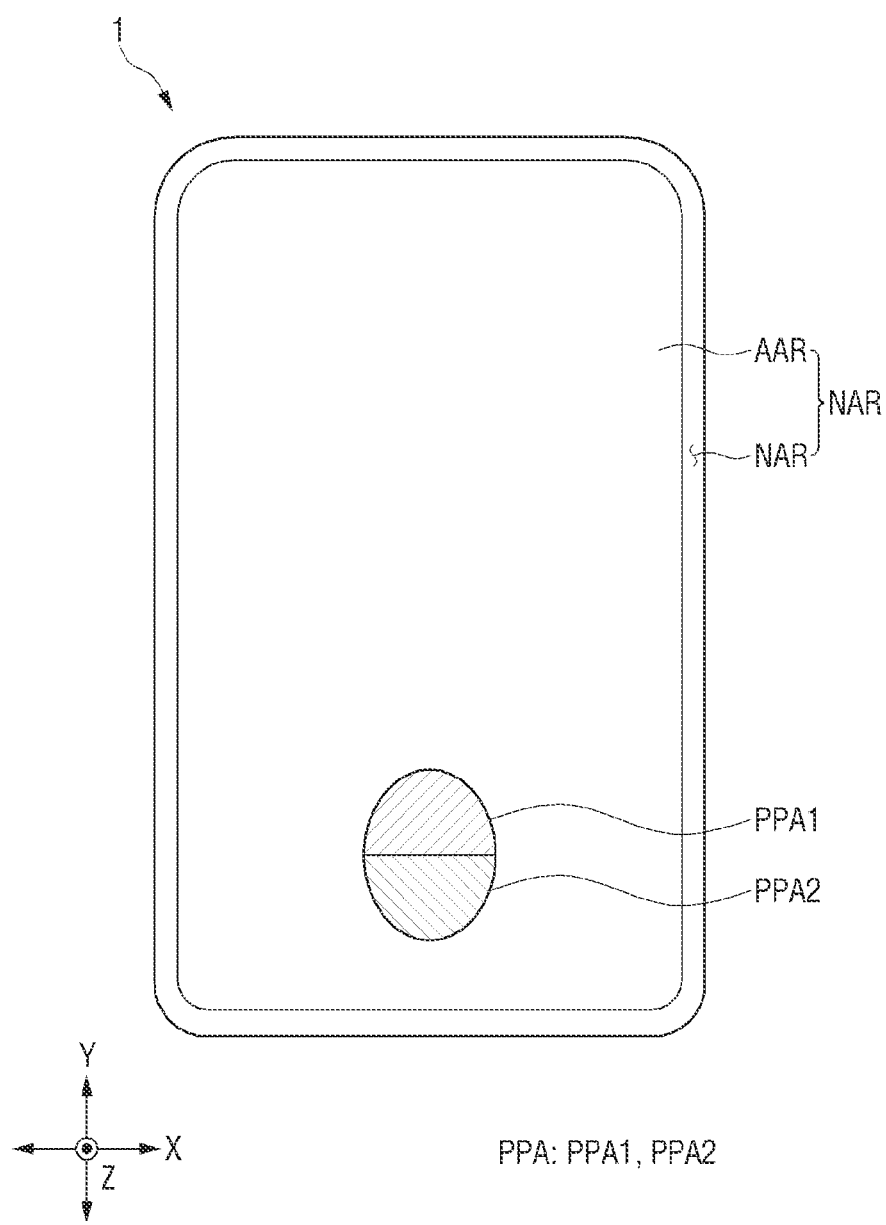
FIG. 11 is a plan view illustrating a blood pressure measurement method using a display device according to another embodiment.

FIG. 11 is a plan view illustrating a blood pressure measurement method using a display device according to another embodiment.

Referring to FIG. 11, the emission area PPA is disposed at (e.g., in or on) a partial area of the display area (e.g., of the active area AAR). In the present embodiment, the emission area PPA has a circular or elliptical shape. The emission area PPA includes a first emission area PPA1 and a second emission area PPA2.

The first emission area PPA1 includes one or more first sub-pixels PX1. The first emission area PPA1 may include the first sub-pixels PX1, as well as the second sub-pixels PX2, the third sub-pixels PX3, and the fourth sub-pixels PX4. However, the present disclosure is not limited thereto, and the first emission area PPA1 may include at least the first sub-pixels PX1, or may include various suitable sub-pixels. When a blood pressure is measured, the first sub-pixels PX1 of the first emission area PPA1 may emit light. The photo-sensors PS may receive reflected light according to the light emitted from the first sub-pixels PX1.

The second emission area PPA2 includes one or more second sub-pixels PX2. The second emission area PPA2 may include the second sub-pixels PX2, as well as the first sub-pixels PX1, the third sub-pixels PX3, and the fourth sub-pixels PX4. However, the present disclosure is not limited thereto, and the second emission area PPA2 may include at least the second sub-pixels PX2, or may include various suitable sub-pixels. When a blood pressure is measured, the second sub-pixels PX2 of the second emission area PPA2 may emit light. The photo-sensors PS may receive reflected light according to the light emitted from the second sub-pixels PX2.

As in the example of the embodiment shown in FIG. 11, each of the first emission area PPA1 and the second emission area PPA2 emits light of different wavelengths, and thus, the photo-sensors PS may receive reflected light according to the light emitted from the first sub-pixels PX1 and the second sub-pixels PX2.

Figure 12:
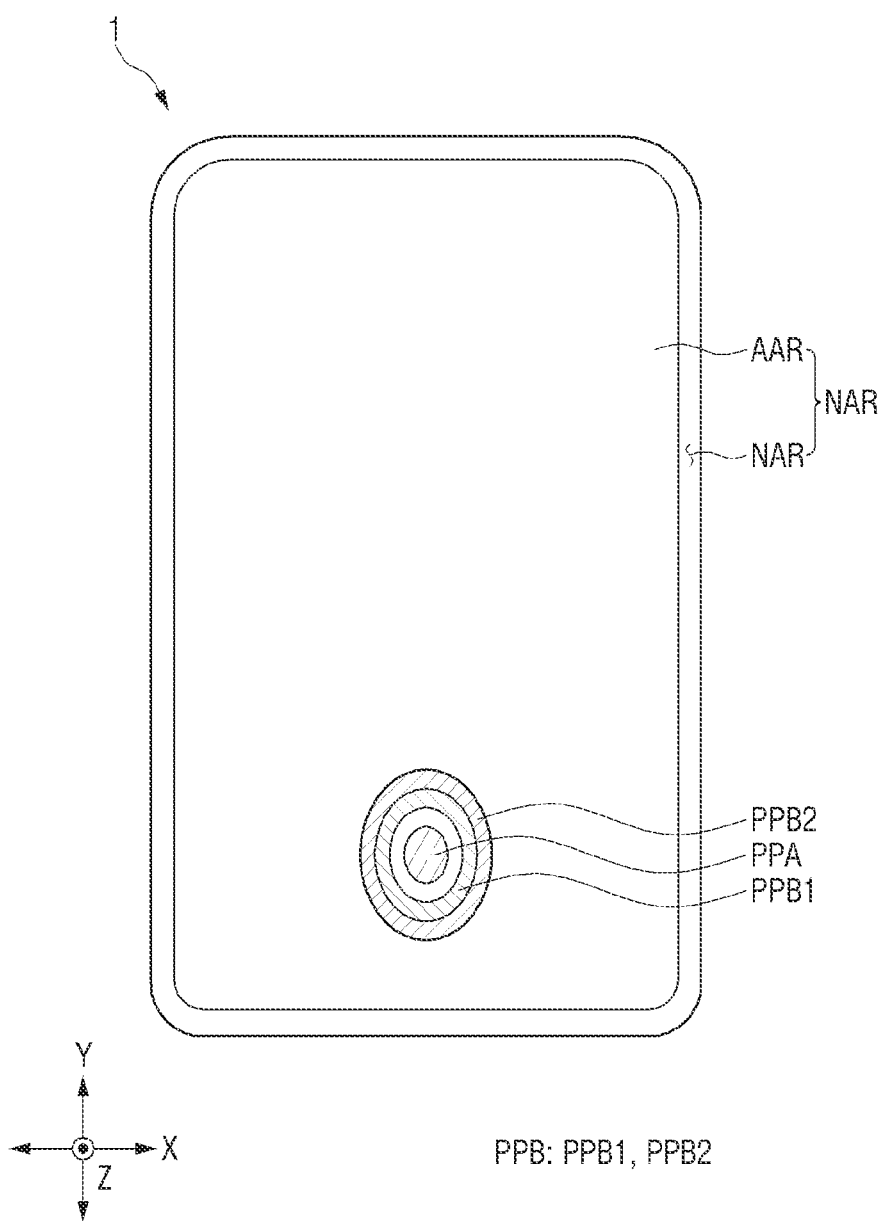
FIG. 12 is a plan view illustrating a blood pressure measurement method using a display device according to another embodiment.
Figure 13:
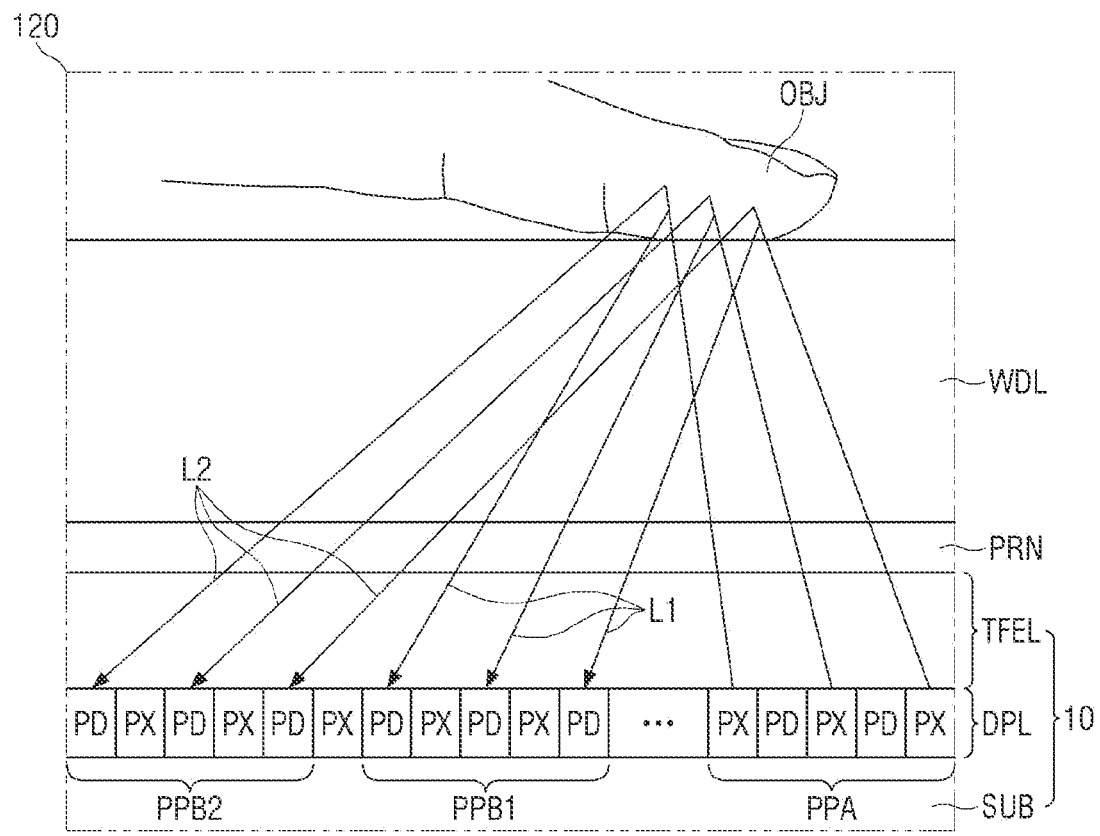
FIG. 13 is a cross-sectional view illustrating the blood pressure measurement method using a display device according to another embodiment.

FIG. 12 is a plan view illustrating a blood pressure measurement method using a display device according to another embodiment. FIG. 13 is a cross-sectional view illustrating the blood pressure measurement method using a display device according to another embodiment.

The embodiments shown in FIGS. 12 and 13 may be different from the embodiments shown in FIGS. 9 and 10, in that a photo-sensor area PPB is disposed to surround (e.g., around a periphery of) the emission area PPA. For example, the emission area PPA shown in FIG. 12 is formed in a circular shape in a plan view, and the photo-sensor area PPB has a donut shape surrounding (e.g., around a periphery of)

the emission area PPA. Also, in the case of the embodiment shown in FIG. 12, a probability that light emitted from the emission area PPA will be received by the photo-sensor area PPB surrounding (e.g., around a periphery of) the emission area PPA may be higher, and thus, excellent light reception efficiency may be exhibited.

The emission area PPA may include the first sub-pixels PX1 and the second sub-pixels PX2. When a blood pressure is measured, the first sub-pixels PX1 and the second sub-pixels PX2 of the emission area PPA may emit light concurrently (e.g., at the same or substantially the same time) with each other.

The photo-sensor area PPB includes a first photo-sensor area PPB1 and a second photo-sensor area PPB2. The first photo-sensor area PPB1 may be disposed to surround (e.g., around a periphery of) the emission area PPA, and the second photo-sensor area PPB2 may be disposed to surround (e.g., around a periphery of) the first photo-sensor area PPB1. The first photo-sensor area PPB1 may be an area for receiving reflected light according to the light emitted from the first sub-pixels PX1, and the second photo-sensor area PPB2 may be an area for receiving reflected light according to the light emitted from the second sub-pixels PX2. Because the wavelength of the light emitted from the first sub-pixels PX1 is shorter than the wavelength of the light emitted from the second sub-pixels PX2, diffraction may occur less in first reflected light L1 of the light emitted from the first sub-pixels PX1 than that in second reflected light L2 of the light emitted from the second sub-pixels PX2. Accordingly, the second photo-sensor area PPB2 is disposed to surround (e.g., around a periphery of) the first photo-sensor area PPB1, such that a light reception probability of the first reflected light L1 and the second reflected light L2 may be increased.

Referring back to FIG. 7, the main processor 800 generates a third pulse wave signal PG3 by removing (or reducing) noise from the second pulse wave signal PG2 based on the first pulse wave signal PG1 and the second pulse wave signal PG2 (S300).

The main processor 800 may remove (or reduce) a noise component included in the second pulse wave signal PG2 using the first pulse wave signal PG1. Consequently, the main processor 800 may generate the third pulse wave signal PG3, in which the noise component for the user is removed or reduced. The third pulse wave signal PG3 with be described in more detail below with reference to FIGS. 14 to 18.

Next, the main processor 800 generates a fourth pulse wave signal PPG1 based on the third pulse wave signal PG3 and the pressure measurement value (S400).

The main processor 800 may generate the fourth pulse wave signal PPG1 through the pressure measurement value and the third pulse wave signal PG3. However, the fourth pulse wave signal PPG1 may vibrate according to a heartbeat cycle, and thus, may reflect a change in blood pressure according to a heartbeat. In this case, because each user may have a different heartbeat cycle, and the fourth pulse wave signal PPG1 may change according to a change in the heartbeat cycle, the fourth pulse wave signal PPG1 may have a different waveform for each user.

The main processor 800 calculates blood pressure information based on the fourth pulse wave signal PPG1 (S500).

The main processor 800 may generate a peak detection signal PPS based on peaks of the fourth pulse wave signal PPG1. The peak detection signal PPS is defined as a signal corresponding to each peak value of one cycle of the pulse wave signal PPG. For example, the peak detection signal PPS (e.g., see FIG. 21) may have one or more peak values PK. Accordingly, the main processor 800 may calculate accurate blood pressure information based on the fourth pulse wave signal PPG1, in which the noise components for the user (e.g., for each user) have been removed (or reduced). This will be described in more detail below with reference to FIGS. 20 and 21.

Figure 14:
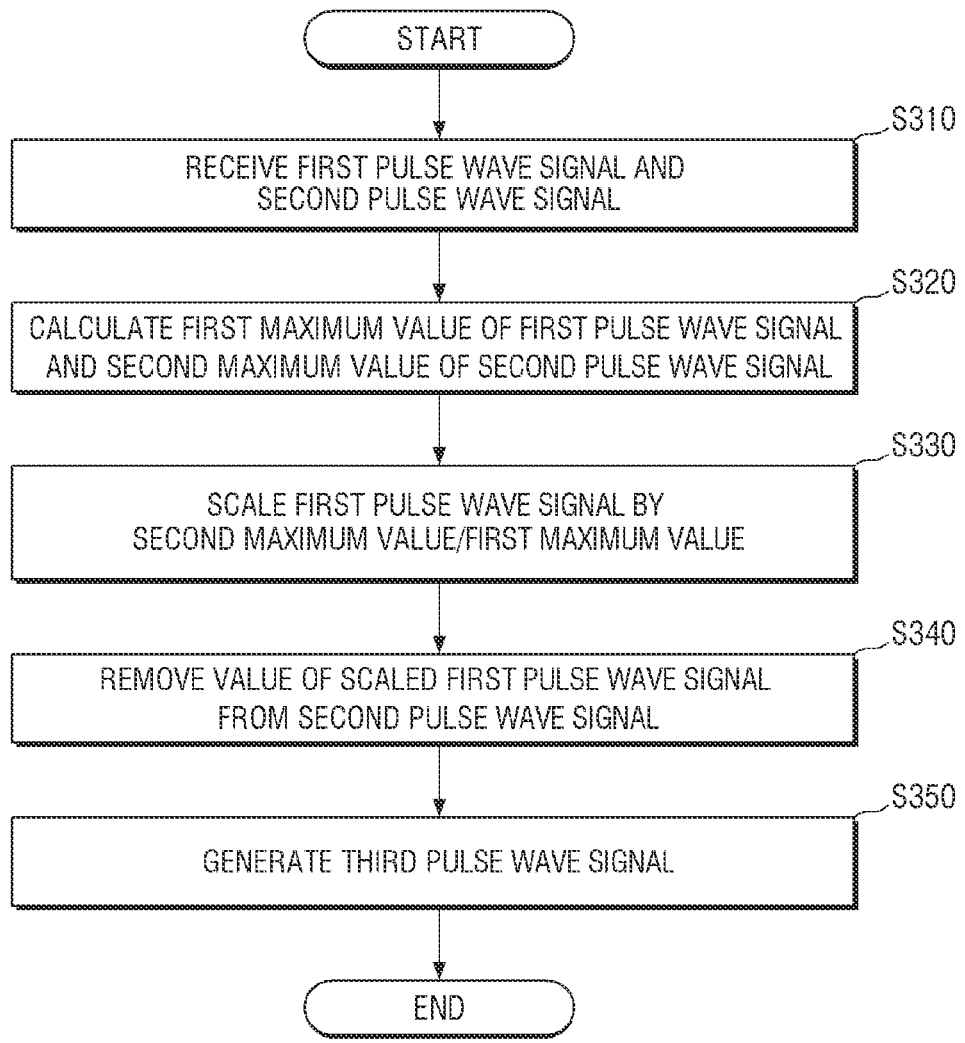
FIG. 14 is a flowchart illustrating a method of generating a third pulse wave signal according to an embodiment.
Figure 15:
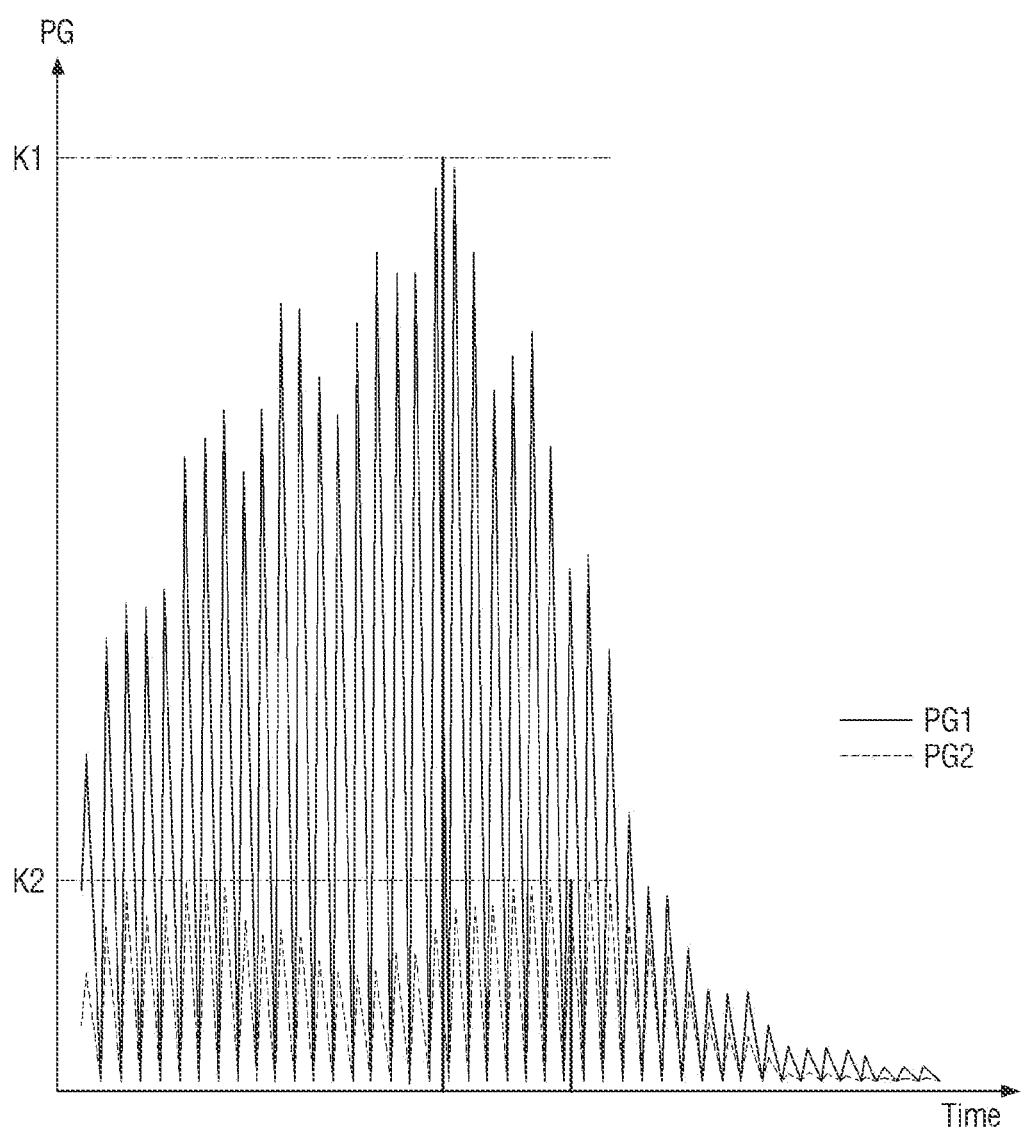
FIGS. 15-17 are graphs illustrating pulse wave signals according to time.
Figure 16:
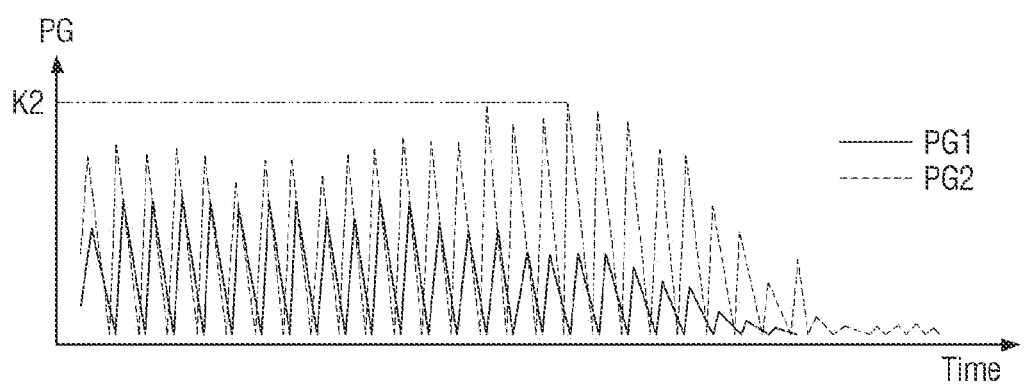
Figure 17:
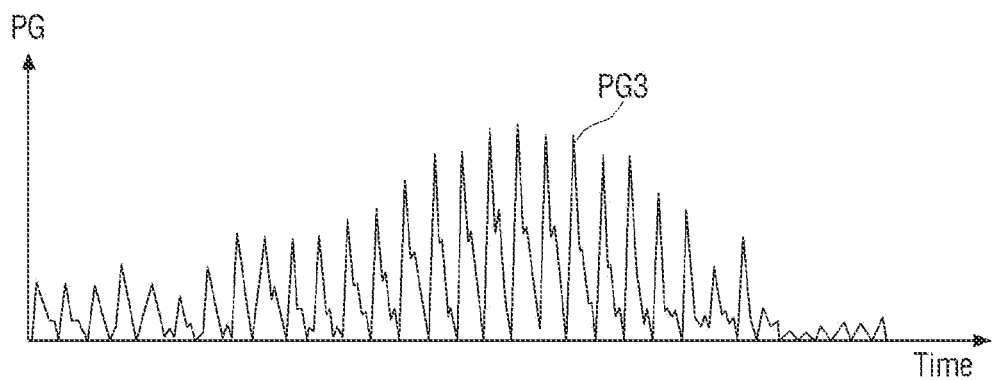

FIG. 14 is a flowchart illustrating a method of generating a third pulse wave signal according to an embodiment. FIGS. 15 through 17 are graphs illustrating pulse wave signals according to a time.

Referring to FIG. 14, first, the main processor 800 receives a first pulse wave signal PG1 and a second pulse wave signal PG2 (S310).

The main processor 800 calculates a first maximum value K1 of the first pulse wave signal PG1, and a second maximum value K2 of the second pulse wave signal PG2 (S320).

Referring to FIG. 15, the main processor 800 calculates the first maximum value K1 of the first pulse wave signal PG1. For example, the first maximum value K1 may be the greatest signal value from among signal values of the first pulse wave signal PG1. In addition, the main processor 800 calculates the second maximum value K2 of the second pulse wave signal PG2. For example, the second maximum value K2 may be the greatest signal value from among signal values of the second pulse wave signal PG2. In this case, because the wavelength of the light emitted from the first sub-pixels PX1 is shorter than the wavelength of the light emitted from the second sub-pixels PX2, also in terms of a magnitude of the reflected light, the first maximum value K1 of the first pulse wave signal PG1 generated by receiving the light of the first sub-pixels PX1 may be greater than the second maximum value K2 of the second pulse wave signal PG2 generated by receiving the light of the second sub-pixels PX2.

Next, the main processor 800 scales the first pulse wave signal PG1 by second maximum value/first maximum value (S330).

Referring further to FIG. 16, the main processor 800 may scale the first pulse wave signal PG1 based on a ratio of the second maximum value K2 to the first maximum value K1. For example, the main processor 800 may decrease a magnitude of the first pulse wave signal PG1 by a value of the second maximum value K2 compared to the first maximum value K1. In this case, a magnitude of the scaled first pulse wave signal PG1 may be smaller than a magnitude of the second pulse wave signal PG2. In addition, a maximum value of the scaled first pulse wave signal PG1 may be the same or substantially the same as the second maximum value K2.

The main processor 800 removes a value of the scaled first pulse wave signal PG1 from the second pulse wave signal PG2 (S340), and generates a third pulse wave signal PG3 (S350).

Referring further to FIG. 17, the main processor 800 may remove the value of the scaled first pulse wave signal PG1 from the second pulse wave signal PG2. In other words, the main processor 800 may generate the third pulse wave signal PG3 in which a noise component existing in the first pulse wave signal PG1 is removed (or reduced). For example, when the first pulse wave signal is defined as PG1, the first maximum value is defined as K1, the second pulse wave signal is defined as PG2, the second maximum value is defined as K2, and the third pulse wave signal is defined as PG3, the third pulse wave signal PG3 may be generated by according to $$PG3 = PG2 - \frac{K3}{K1}PG1. \qquad \text{Equation 1}$$

In the present embodiment, a noise component included in the second pulse wave signal PG2 may be removed (or reduced) using the first pulse wave signal PG1. Accordingly, the third pulse wave signal PG3 in which the noise component for the user (e.g., for each user) is removed may be generated, and the blood pressure information may be accurately calculated.

Figure 18:
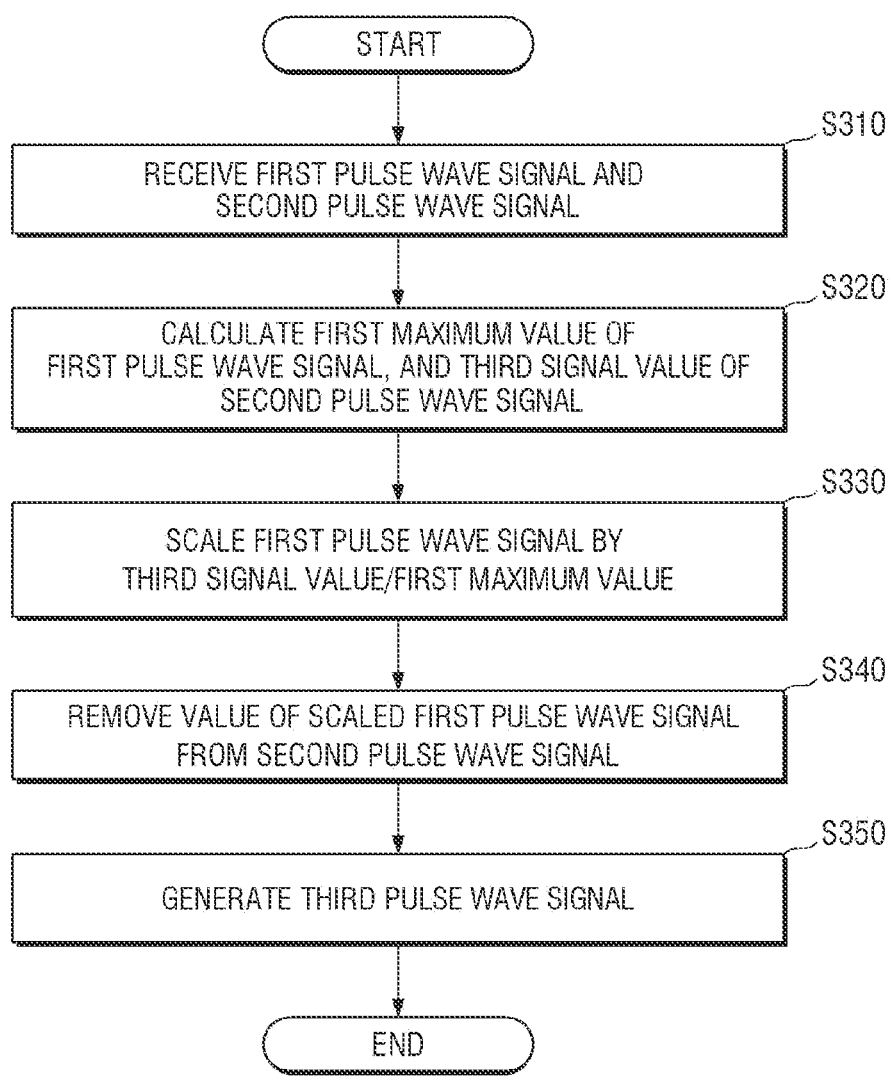
FIG. 18 is a flowchart illustrating a method of generating a third pulse wave signal according to another embodiment.
Figure 19:
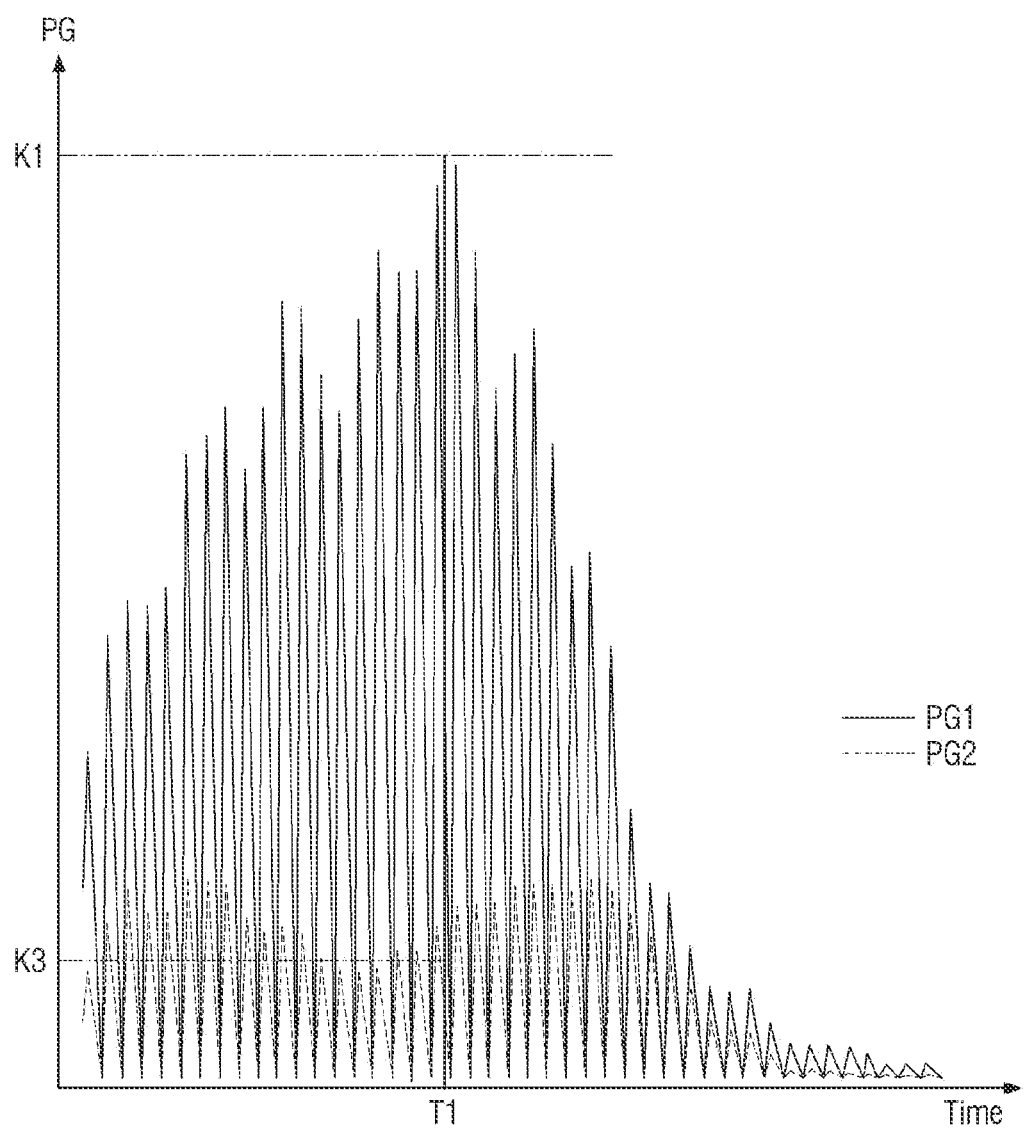
FIG. 19 is a graph illustrating a pulse wave signal according to time.

FIG. 18 is a flowchart illustrating a method of generating a third pulse wave signal according to another embodiment. FIG. 19 is a graph illustrating a pulse wave signal according to a time.

The embodiments illustrated in FIGS. 18 and 19 may be the same or substantially the same as the embodiments illustrated in FIGS. 14 to 17, except that a method of scaling the first pulse wave signal may be different, and thus, redundant description thereof may not be repeated.

Referring to FIG. 18, first, the main processor 800 receives a first pulse wave signal PG1 and a second pulse wave signal PG2 (S310). The main processor 800 calculates a first maximum value K1 of the first pulse wave signal PG1 and a third signal value K3 of the second pulse wave signal PG2 (S320).

Referring to FIG. 19, the main processor 800 calculates the first maximum value K1 of the first pulse wave signal PG1. For example, the first maximum value K1 may be the greatest signal value from among signal values of the first pulse wave signal PG1. In addition, the main processor 800 calculates a first section in which the first pulse wave signal PG1 has the first maximum value K1. The main processor 800 calculates the third signal value K3 of the second pulse wave signal PG2. For example, the third signal value K3 may be a signal value of the second pulse wave signal PG2 corresponding to (e.g., overlapping with) the first section from among signal values of the second pulse wave signal PG2. In this case, because the wavelength of light emitted from the first sub-pixels PX1 is shorter than the wavelength of light emitted from the second sub-pixels PX2, also in terms of a magnitude of the reflected light, the first maximum value K1 of the first pulse wave signal PG1 generated by receiving the light of the first sub-pixels PX1 may be greater than the third signal value K3 of the second pulse wave signal PG2 generated by receiving the light of the second sub-pixels PX2.

Next, the main processor 800 scales the first pulse wave signal PG1 by the third signal value/first maximum value (S330).

The main processor 800 may scale the first pulse wave signal PG1 based on a ratio of the third signal value K3 to the first maximum value K1. For example, the main processor 800 may decrease a magnitude of the first pulse wave signal PG1 by a value of the third signal value K3 compared to the first maximum value K1. In this case, a magnitude of the scaled first pulse wave signal PG1 may be smaller than a magnitude of the second pulse wave signal PG2. In addition, a maximum value of the scaled first pulse wave signal PG1 may be the same or substantially the same as the third signal value K3.

The main processor 800 removes (or reduces) a value of the scaled first pulse wave signal PG1 from the second pulse wave signal PG2 (S340), and generates a third pulse wave signal PG3 (S350).

Referring further to FIG. 17, the main processor 800 may remove the value of the scaled first pulse wave signal PG1 from the second pulse wave signal PG2. In other words, the main processor 800 may generate the third pulse wave signal PG3 in which a noise component existing in the first pulse wave signal PG1 is removed (or reduced). For example, when the first pulse wave signal is defined as PG1, the first maximum value is defined as K1, the second pulse wave signal is defined as PG2, the third signal value is defined as K3, and the third pulse wave signal is defined as PG3, the third pulse wave signal PG3 may be generated according to $$PG3 = PG2 - \frac{K2}{K1}PG1 \qquad \text{Equation 2}$$
$$PG3 = PG2 - \frac{K3}{K1}PG1.$$

Also, in an embodiment, a noise component included in the second pulse wave signal PG2 may be removed (or reduced) using the first pulse wave signal PG1. Accordingly, the third pulse wave signal PG3 in which the noise component for the user (e.g., for each user) is removed may be generated, and the blood pressure information may be accurately calculated.

Figure 20:
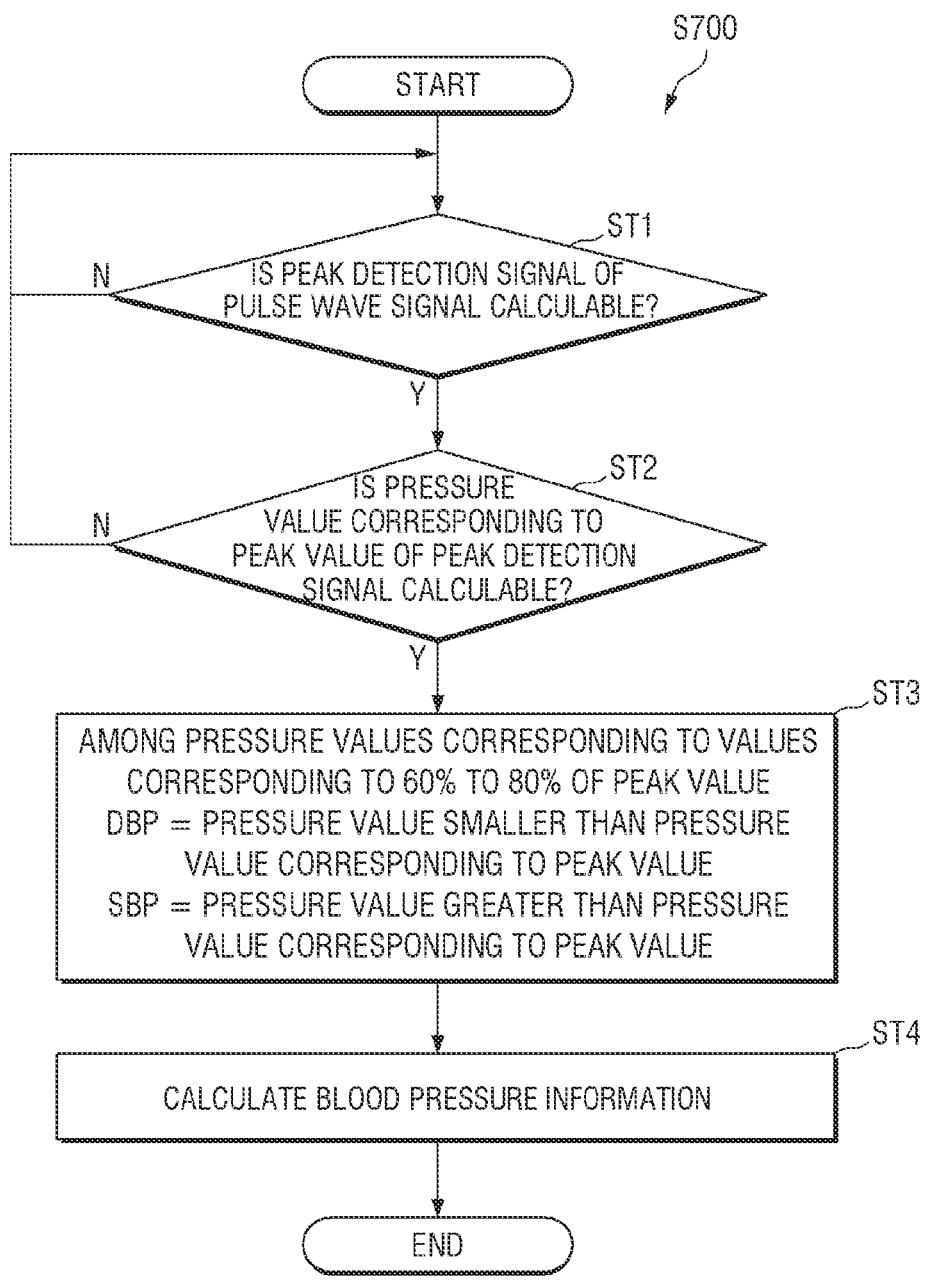
FIG. 20 is a flowchart illustrating a method of calculating a blood pressure using a generated pulse wave signal.
Figure 21:
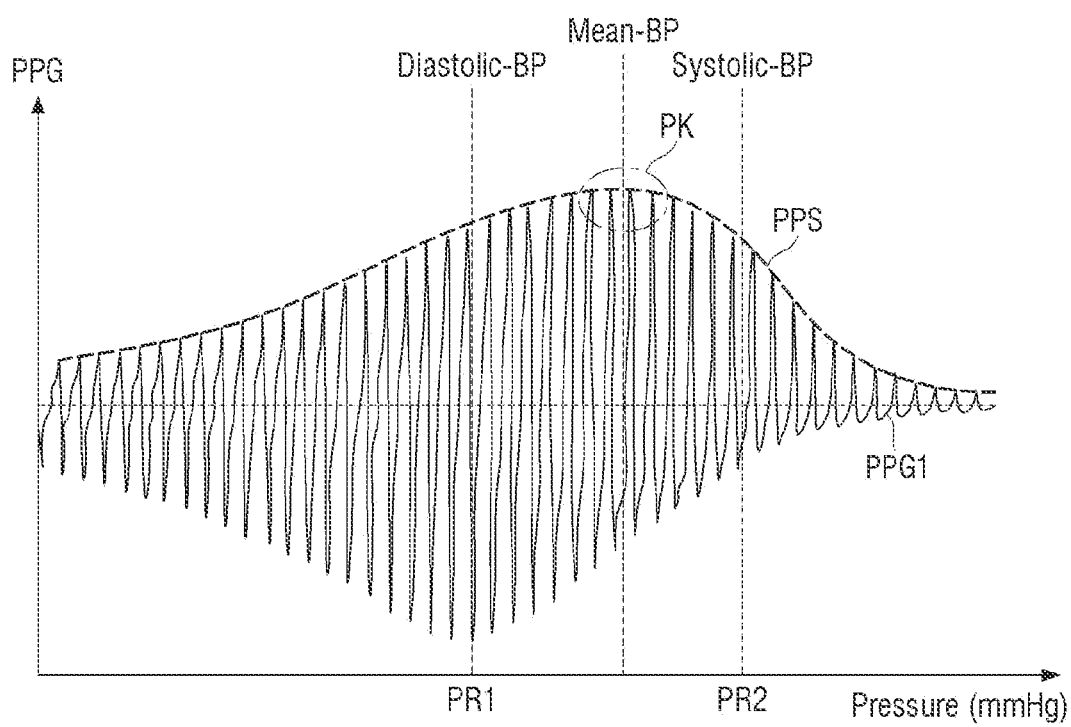
FIG. 21 is a graph illustrating the method of calculating a blood pressure using a generated pulse wave signal.

FIG. 20 is a flowchart illustrating a method of calculating a blood pressure using a generated pulse wave signal. FIG. 21 is a graph illustrating the method of calculating a blood pressure using a generated pulse wave signal.

A method of calculating blood pressure information based on the fourth pulse wave signal PPG1 will be described in more detail with reference to FIGS. 20 and 21.

Referring further to FIGS. 20 and 21, first, the main processor 800 determines whether or not the peak detection signal PPS is calculable (ST1). For example, the main first processor 800 may determine whether or not the peak detection signal PPS may be calculated based on the fourth pulse wave signal PPG1.

The main processor 800 may generate the peak detection signal PPS using peaks of the fourth pulse wave signal PPG1. The peak detection signal PPS is defined as a signal corresponding to each peak value of one cycle of the fourth pulse wave signal PPG1. For example, the fourth pulse wave signal PPG1 may have one or more peak values. The main processor 800 may calculate the peak detection signal PPS including points corresponding to the peak values of the fourth pulse wave signal PPG1.

Next, the main processor 800 determines whether or not a pressure value corresponding to the peak value PK of the peak detection signal PPS may be calculated (ST2).

When a peak of the peak detection signal PPS exists, the main processor 800 may calculate a pressure value corresponding to the peak value PK of the peak detection signal PPS.

Next, the main processor 800 calculates a systolic blood pressure SBP, a diastolic blood pressure DBP, and the like, based on the peak value PK of the peak detection signal PPS (ST3), and calculates blood pressure information (ST4).

The main processor 800 may calculate the diastolic blood pressure DBP lower than the pressure value, the systolic blood pressure SBP higher than the pressure value, and a mean blood pressure according to the pressure value. For example, the main processor 800 may calculate pressure values corresponding to values corresponding to 60% to 80% of the peak value PK. The main processor 800 may calculate a pressure value smaller than a pressure value corresponding to the peak value PK from among the pressure values as a first pressure value PR1. In addition, the main processor 800 may calculate the first pressure value PR1 as the diastolic blood pressure DBP. In addition, the main processor 800 may calculate a pressure value greater than the pressure value corresponding to the peak value PK from among the pressure values as a second pressure value PR2. In addition, the main processor 800 may calculate the second pressure value PR2 as the systolic blood pressure SBP.

In an embodiment, the pulse wave signal PPG vibrates according to the heartbeat cycle, and thus, may reflect a change in blood pressure according to the heartbeat. In this case, because each user has a different heartbeat cycle, and the pulse wave signal changes according to a change in the heartbeat cycle, each user may have a different pulse wave signal. Accordingly, the display device generates the first pulse wave signal PG1 and the second pulse wave signal PG2 generated by the light emitted from each of the first and second sub-pixels to effectively remove (or reduce) different noise components for the user (e.g., for each user), such that a blood pressure may be accurately calculated.

Figure 22:
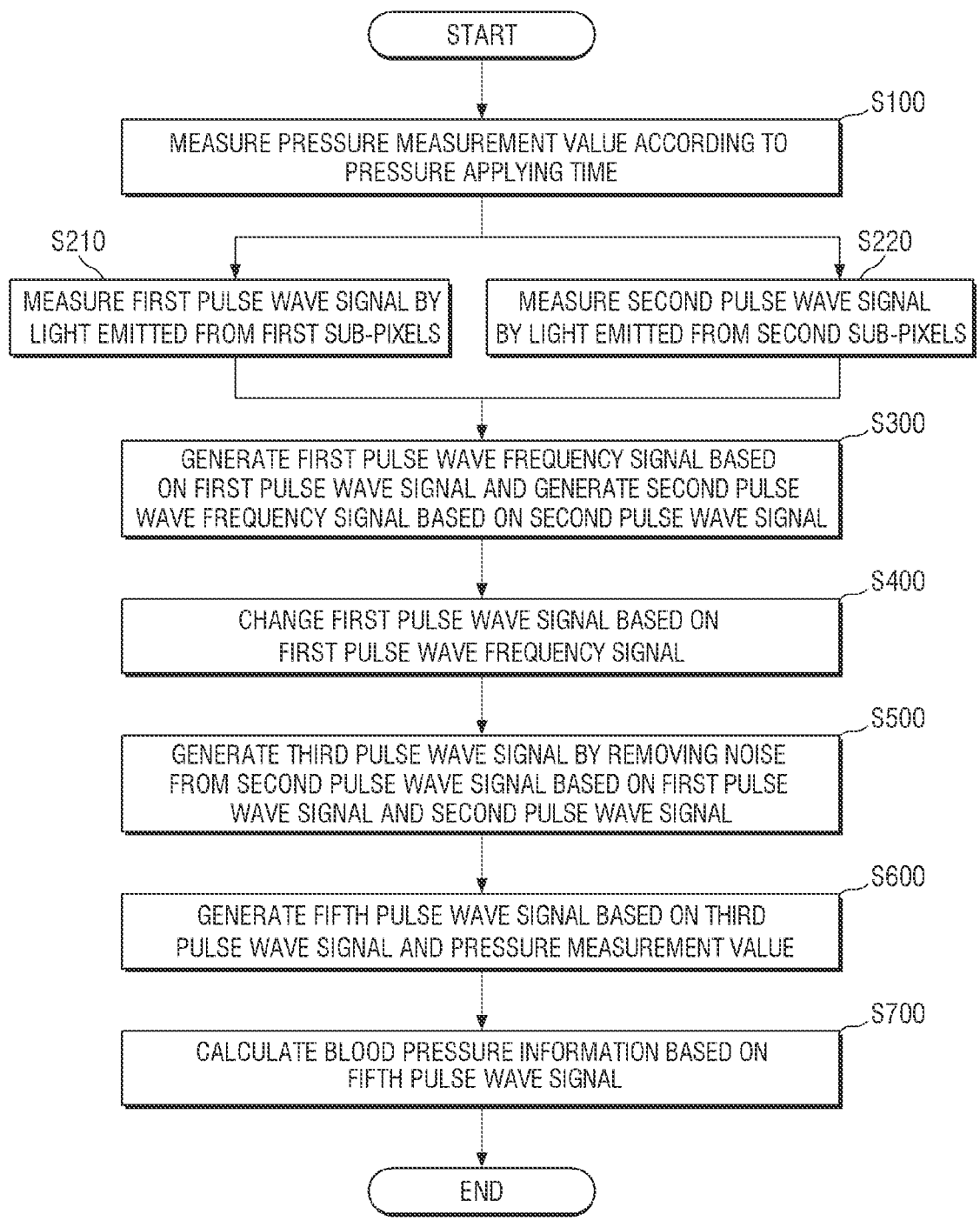
FIG. 22 is a flowchart illustrating a blood pressure measurement method using a display device according to another embodiment.
Figure 23:
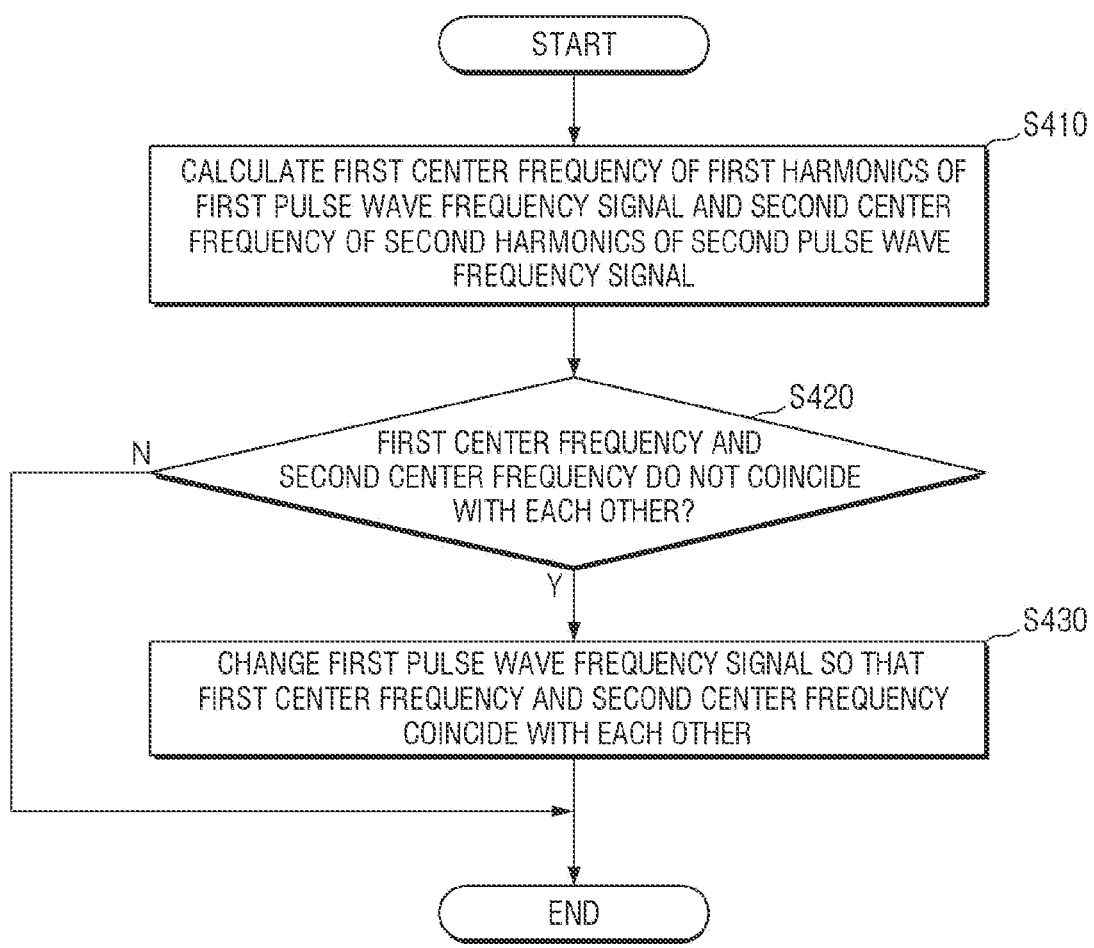
FIG. 23 is a flowchart illustrating a method of changing a first pulse wave signal according to another embodiment.
Figure 24:
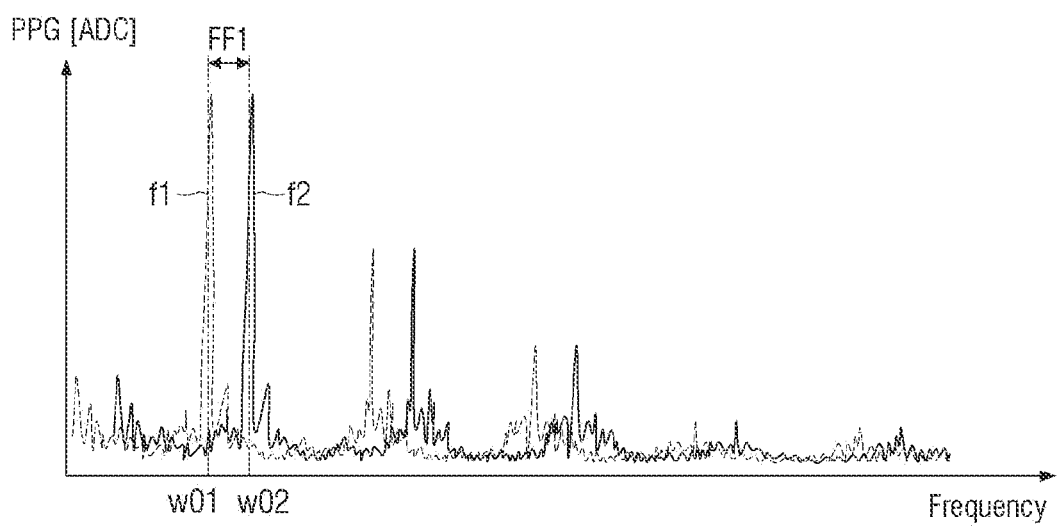
FIG. 24 is a graph illustrating the method of changing a first pulse wave signal according to another embodiment.
Figure 25:
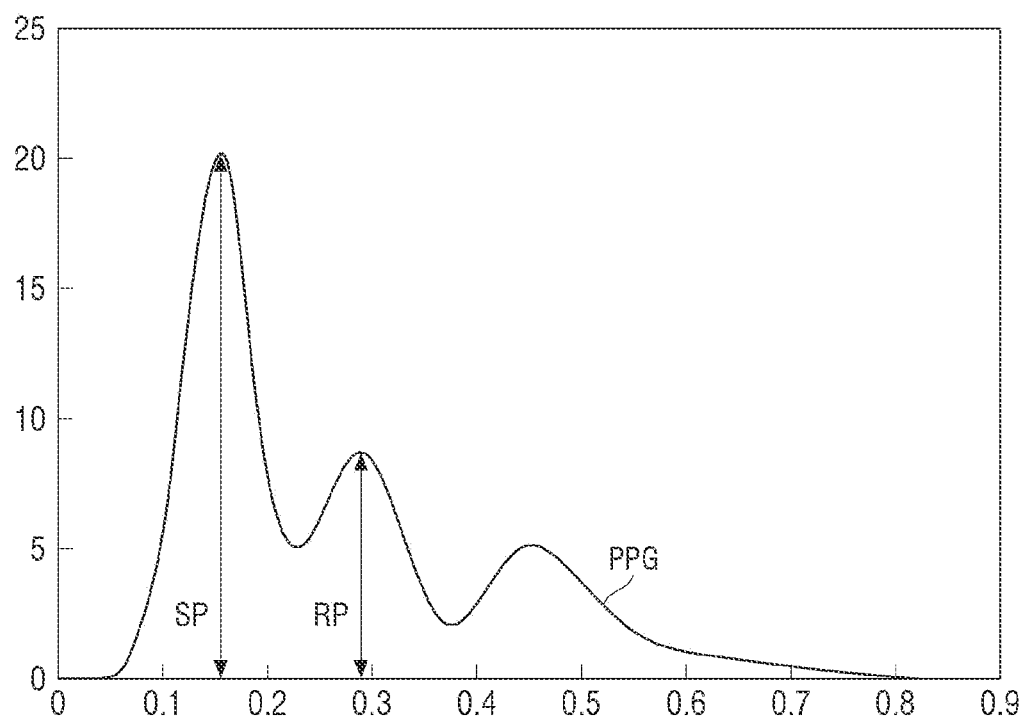
FIGS. 25-27 are enlarged graphs of a waveform of one cycle of a pulse wave signal.
Figure 26:
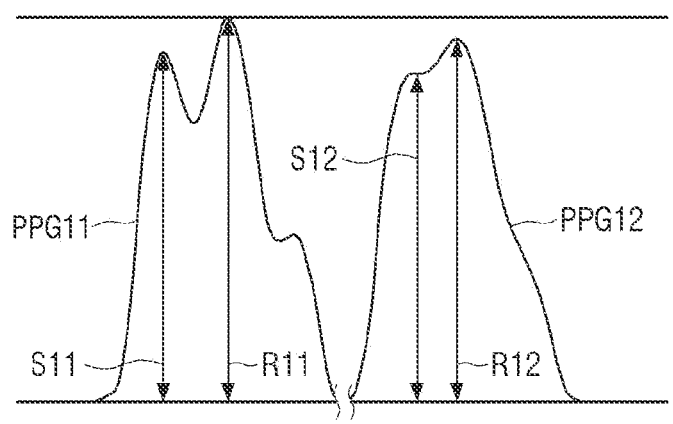
Figure 27:
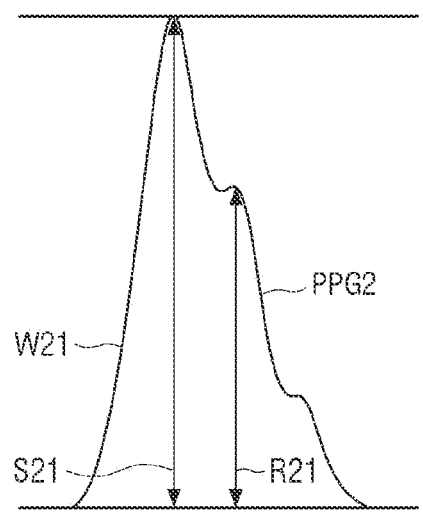

FIG. 22 is a flowchart illustrating a blood pressure measurement method using a display device according to another embodiment. FIG. 23 is a flowchart illustrating a method of changing a first pulse wave signal PG1 according to another embodiment. FIG. 24 is a graph illustrating the method of changing a first pulse wave signal PG1 according to another embodiment. FIGS. 25 through 27 are enlarged graphs of a waveform of one cycle of a pulse wave signal.

The embodiments of FIGS. 22 to 27 may be the same or substantially the same as the embodiments described above with reference to FIGS. 7 to 13, except that a method of scaling the first wave pulse signal PG1 may be different. Accordingly, redundant description thereof may not be repeated.

Referring to FIG. 22, first, as described above with reference to FIG. 7, the pressure sensing circuit 40 measures a pressure measurement value according to a pressure applying time (S100), the pulse wave sensing circuit 50 measures a first pulse wave signal PG1 generated by light emitted from the first sub-pixels PX1 (S210), and the pulse wave sensing circuit 50 measures a second pulse wave signal PG2 generated by light emitted from the second sub-pixels PX2 (S220). Next, the main processor 800 generates a first pulse wave frequency signal FP1 based on the first pulse wave signal PG1, and generates a second pulse wave frequency signal FP2 based on the second pulse wave signal PG2 (S300).

Referring further to FIG. 23, the main processor 800 calculates a first center frequency W01 of first harmonics f1 of the first pulse wave frequency signal FP1, and a second center frequency W02 of second harmonics f2 of the second pulse wave frequency signal FP2 (S410).

Referring further to FIG. 24, the main processor 800 may calculate the first harmonics f1 of the first pulse wave frequency signal FP1. The first harmonics f1 may be the highest peak in the first pulse wave frequency signal FP1. In addition, the main processor 800 may calculate the first center frequency W01 of the first harmonics f1. The main processor 800 may calculate the second harmonics f2 of the second pulse wave frequency signal FP2. The second harmonics f2 may be the highest peak in the second pulse wave frequency signal FP2. In addition, the main processor 800 may calculate the second center frequency W02 of the second harmonics f2.

Referring back to FIG. 23, next, the main processor 800 determines whether or not the first center frequency W01 and the second center frequency W02 do not coincide with each other (S420).

The first center frequency W01 and the second center frequency W02 may not coincide with each other. For example, the first center frequency W01 and the second center frequency W02 may have a difference corresponding to a first frequency FF1 therebetween.

When the first center frequency W01 and the second center frequency W02 do not coincide with each other (e.g., YES at S420), the main processor 800 changes the first pulse wave frequency signal FP1, so that the first center frequency W01 and the second center frequency W02 coincide with each other (S430).

For example, when the first center frequency W01 and the second center frequency W02 has the difference corresponding to the first frequency FF1 therebetween, the main processor 800 may change the first pulse wave frequency signal FP1 by the first frequency FF1. Accordingly, the first center frequency W01 and the second center frequency W02 may coincide with each other.

Referring back to FIG. 22, the main processor 800 changes the first pulse wave signal PG1 based on the first pulse wave frequency signal FP1 (S400).

The main processor 800 may also change the first pulse wave signal PG1 by a time corresponding to the first frequency based on the first pulse wave frequency signal FP1 changed by the first frequency. Accordingly, measurement time errors of peak waveforms of the first pulse wave signal PG1 and the second pulse wave signal PG2 may be decreased.

Next, the main processor 800 generates the third pulse wave signal PG3 by removing (or reducing) noise from the second pulse wave signal PG2 based on the first pulse wave signal PG1 and the second pulse wave signal PG2 (S500), which may be the same or substantially the same as described above with reference to FIGS. 7 through 13 (e.g., see S300 in FIG. 7), and thus, redundant description thereof will not be repeated.

Next, the main processor 800 generates a fifth pulse wave signal PPG2 based on the third pulse wave signal PG3 and the pressure measurement value (S600). This will be described in more detail below with reference to FIGS. 25 through 27.

The main processor 800 divides a wave cycle of the fifth pulse wave signal PPG2 according to a period in which a wave according to a heartbeat and a reflected wave of a blood vessel are sequentially generated. For example, one cycle of the fifth pulse wave signal PPG2 may include a plurality of waveforms having different amplitudes from one another. Accordingly, when a peak value SP of a waveform having the greatest amplitude from among the plurality of waveforms is defined as a pulse wave contraction value, and a peak value RP of a waveform having the second greatest amplitude from among the plurality of waveforms is defined as a reflected pulse wave value, the pulse wave contraction value is defined as Sp, the reflected pulse wave value is defined as Rp, and the reflected pulse wave ratio is defined as RI, such that the reflected pulse wave ratio RI may be calculated according to Equation 3.

$$RI = \frac{R_P}{S_P} \qquad \text{Equation 3}$$

Here, when the fifth pulse wave signal PPG2 is inaccurate, the reflected pulse wave ratio RI may have a value of 1 or more, and when the fifth pulse wave signal PPG2 is suitable (e.g., is accurate or ideal), the reflected pulse wave ratio RI may have a value of 1 or less.

The main processor 800 may change the reflected pulse wave ratio RI of the fifth pulse wave signal PPG2 by removing (or reducing) the noise for the user (e.g., for each user) to generate the second pulse wave signal PG2. For example, FIG. 26 shows a graph illustrating a third pulse wave signal PPG11 cycle and a fourth pulse wave signal PPG12 cycle according to a third pulse wave frequency signal FP3. FIG. 26 illustrates an example in which reflected pulse wave values R11 and R12 are detected to be greater than pulse wave contraction values S11 and S12 of the third pulse wave signal PPG11 cycle and the fourth pulse wave signal PPG12 cycle. In other words, reflected pulse wave ratios RI of the third pulse wave signal PPG11 cycle and the fourth pulse wave signal PPG12 cycle are 1 or more. On the other hand, as in the case shown in FIG. 27, when the main processor 800 generates the fifth pulse wave signal PPG2 by changing the reflected pulse wave ratio RI, the reflected pulse wave ratio RI of the fifth pulse wave signal PPG2 cycle is 1 or less.

According to one or more embodiments of the present disclosure, the main processor 800 may change the reflected pulse wave ratio RI of the fifth pulse wave signal PPG2, so as to be greater than 1 by removing (or reducing) the noise for the user (e.g., for each user). Accordingly, noise components for the user (e.g., for each user) are blocked or reduced, and thus, accuracy of the blood pressure calculation based on the reflected pulse wave ratio RI may be improved.

Referring back to FIG. 22, the main processor 800 calculates blood pressure information based on the fifth pulse wave signal PPG2 (S700). A method of calculating the blood pressure information using the reflected pulse wave ratio will be described in more detail below with reference to FIGS. 28 and 29.

Figure 28:
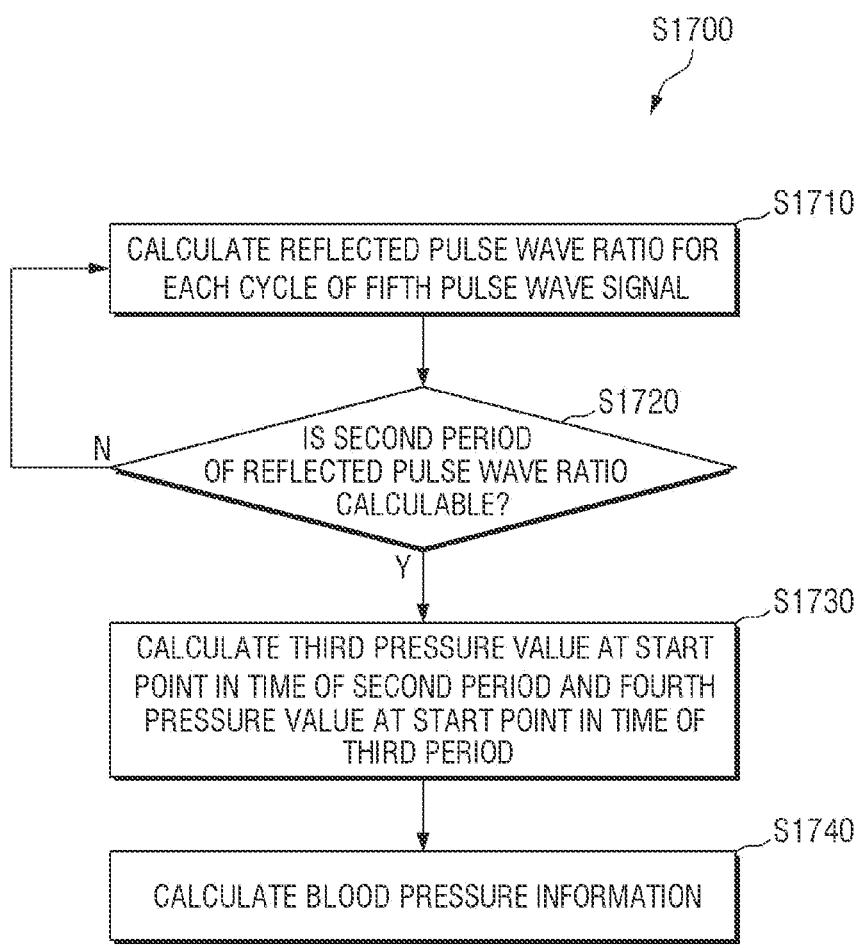
FIG. 28 is a flowchart illustrating a method of calculating a blood pressure using a generated pulse wave signal according to another embodiment.
Figure 29:
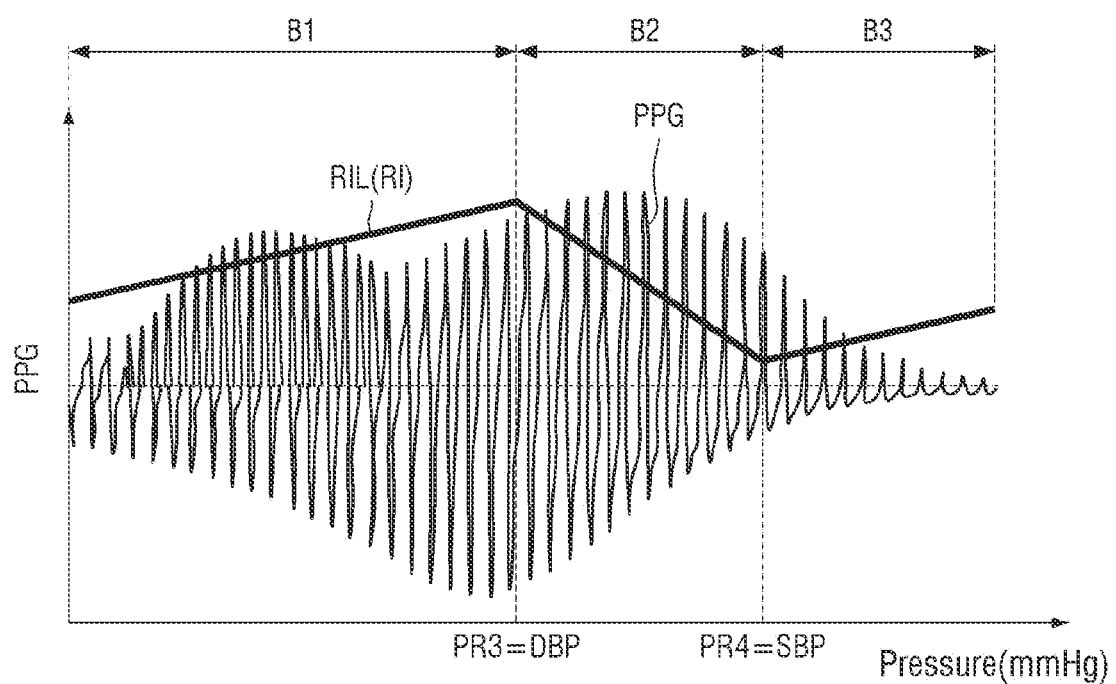
FIG. 29 is a graph illustrating the method of calculating a blood pressure using a generated pulse wave signal according to another embodiment.

FIG. 28 is a flowchart illustrating a method of calculating a blood pressure using a generated pulse wave signal according to another embodiment. FIG. 29 is a graph illustrating the method of calculating a blood pressure using a generated pulse wave signal according to another embodiment.

Referring to FIGS. 28 and 29, first, a reflected pulse wave ratio RI is calculated for each cycle of the fifth pulse wave signal PPG2 (S1710). The reflected pulse wave ratio RI is the same or substantially the same as the reflected pulse wave ratio RI described above with reference to FIGS. 25 to 27, and thus, redundant description thereof will not be repeated.

Next, the main processor 800 determines whether or not a second period B2 of the reflected pulse wave ratio RI may be calculated (S1720).

The main processor 800 sequentially stores detection results of reflected pulse wave ratios RI of reflected pulse waves to pulse wave contraction values, and analyzes the stored reflected pulse wave ratios RI. The main processor 800 may continuously make changes in magnitude of the reflected pulse wave ratios RI data to analyze a change in magnitude of reflected pulse wave ratio data RIL(RI).

The reflected pulse wave ratio RI includes a first period B1 in which the reflected pulse wave ratio RI fluctuates within a first range, a second period B2 in which the reflected pulse wave ratio RI fluctuates within a second range, and a third period B3 in which the reflected pulse wave ratio RI fluctuates within a third range. For example, the main processor 800 may analyze a reflected pulse wave ratio signal RIL to analyze a first period B1 in which the reflected pulse wave ratio RI is gently changed within a suitable range (e.g., a predetermined or preset range) in a saturated state, a second period B2 in which the reflected pulse wave ratio RI is sharply decreased or increased in a suitable range (e.g., a predetermined or preset range) within a suitable period (e.g., a predetermined or preset period), a third period B3 in which the reflected pulse wave ratio RI is gently changed within a suitable range (e.g., a predetermined or preset range) in a saturated state again after it is sharply decreased or increased, and/or the like.

Here, a width of the first range and a width of the third range may be smaller than a width of the second range. In addition, a gradient of the second period B2 of the reflected pulse wave ratio RI may be greater than a gradient of the first period B1 of the reflected pulse wave ratio RI and a gradient of the third period B3 of the reflected pulse wave ratio RI.

The main processor 800 calculates a systolic blood pressure SBP, a diastolic blood pressure DBP, and the like, based on the reflected pulse wave ratio RI (S1730), and calculates the blood pressure information (S1740).

The main processor 800 may analyze the reflected pulse wave ratio RI to detect a start point in time of the second period B2. In addition, the main processor 800 may calculate a third pressure value PR3 corresponding to the fifth pulse wave signal PPG2 at the start point in time of the second period B2. The main processor 800 may calculate the third pressure value PR3 as the diastolic blood pressure DBP. In addition, the main processor 800 may analyze the reflected pulse wave ratio RI to detect a start point in time of the third period B3 after the second period B2. In addition, the main processor 800 may calculate a fourth pressure value PR4 corresponding to the fifth pulse wave signal PPG2 at the start point in time of the third period B3. The main processor 800 may calculate the fourth pressure value PR4 as the systolic blood pressure SBP.

Referring to FIG. 29, an example in which the reflected pulse wave ratio data RIL(RI) is accurately calculated is illustrated. As in the case of FIG. 29, the main processor 800 may block (or reduce) the noise for the user (e.g., for each user). In other words, the main processor 840 may generate the fifth pulse wave signal PPG2, so as to accurately calculate the reflected pulse wave ratio data RIL(RI). Accordingly, noise components for the user (e.g., for each user) are blocked or reduced, and thus, accuracy of the blood pressure calculation based on the pulse wave ratio RI may be improved.

Although some embodiments have been described, those skilled in the art will readily appreciate that various modifications are possible in the embodiments without departing from the spirit and scope of the present disclosure. It will be understood that descriptions of features or aspects within each embodiment should typically be considered as available for other similar features or aspects in other embodiments, unless otherwise described. Thus, as would be apparent to one of ordinary skill in the art, features, characteristics, and/or elements described in connection with a particular embodiment may be used singly or in combination with features, characteristics, and/or elements described in connection with other embodiments unless otherwise specifically indicated. Therefore, it is to be understood that the foregoing is illustrative of various example embodiments and is not to be construed as limited to the specific embodiments disclosed herein, and that various modifications to the disclosed embodiments, as well as other example embodiments, are intended to be included within the spirit and scope of the present disclosure as defined in the appended claims, and their equivalents.

What is claimed is:

1. A blood pressure measurement method using a display device,
the display device comprising:
a display panel comprising first sub-pixels to emit light of a first color, and second sub-pixels to emit light of a second color;
a pressure sensor to sense a pressure applied from the outside; and
a photo-sensor to sense light,
the method comprising:
generating a first pulse wave signal according to light emitted by the first sub-pixels and sensed by the photo-sensor;
generating a second pulse wave signal according to light emitted by the second sub-pixels and sensed by the photo-sensor;
generating a third pulse wave signal by removing noise from the second pulse wave signal based on the first pulse wave signal, the second pulse wave signal, and a maximum value of the first pulse wave signal; and
calculating blood pressure information based on the third pulse wave signal and a pressure measurement value sensed by the pressure sensor, wherein the blood pressure information is displayed on the display panel.

2. The blood pressure measurement method of claim 1, wherein the generating of the third pulse wave signal comprises:
calculating a first maximum value of the first pulse wave signal and a second maximum value of the second pulse wave signal; and
generating the third pulse wave signal based on a ratio of the second maximum value to the first maximum value.

3. The blood pressure measurement method of claim 2, wherein the third pulse wave signal is generated according to $$PG3 = PG2 - \frac{K2}{K1}PG1,$$

where PG1 is the first pulse wave signal, K1 is the first maximum value, PG2 is the second pulse wave signal, K2 is the second maximum value, and PG3 is the third pulse wave signal.

4. The blood pressure measurement method of claim 1, wherein the generating of the third pulse wave signal comprises:
calculating a first maximum value of the first pulse wave signal;
calculating a first section of the first maximum value;
calculating a third maximum value of the second pulse wave signal in the first section; and
generating the third pulse wave signal based on a ratio of the third maximum value to the first maximum value.

5. The blood pressure measurement method of claim 4, wherein the third pulse wave signal is generated according to $$PG3 = PG2 - \frac{K3}{K1}PG1,$$

where PG1 is the first pulse wave signal, K1 is the first maximum value, PG2 is the second pulse wave signal, K3 is the third maximum value, and PG3 is the third pulse wave signal.

6. The blood pressure measurement method of claim 1, wherein a wavelength of the light of the first color emitted by the first sub-pixels is smaller than a wavelength of the light of the second color emitted by the second sub-pixels.

7. The blood pressure measurement method of claim 6, wherein the light of the first color emitted by the first sub-pixels is green light, and the light of the second color emitted by the second sub-pixels is red light.

8. The blood pressure measurement method of claim 6, wherein the first sub-pixels and the second sub-pixels are configured to alternately emit light with each other, and the photo-sensor is configured to alternately sense the light emitted by the first sub-pixels and the light emitted by the second sub-pixels.

9. The blood pressure measurement method of claim 6, wherein the photo-sensor comprises:
a first photo-sensor area configured to sense the light of the first color emitted by the first sub-pixels; and
a second photo-sensor area configured to sense the light of the second color emitted by the second sub-pixels, and
wherein the first sub-pixels and the second sub-pixels are surrounded by the first photo-sensor area.

10. The blood pressure measurement method of claim 9, wherein the first photo-sensor area is surrounded by the second photo-sensor area.

11. The blood pressure measurement method of claim 1, wherein the calculating of the blood pressure information comprises:
generating a fourth pulse wave signal based on the third pulse wave signal and the pressure measurement value;
generating a peak detection signal based on peak values of the fourth pulse wave signal;
calculating a pressure value corresponding to a peak value of the peak detection signal; and
calculating a diastolic blood pressure lower than the pressure value, a systolic blood pressure higher than the pressure value, and a mean blood pressure according to the pressure value.

12. The blood pressure measurement method of claim 11, wherein a first pressure value smaller than the pressure value corresponding to 60% to 80% of the peak value in the peak detection signal is calculated as the diastolic blood pressure, and a second pressure value greater than the pressure value is calculated as the systolic blood pressure.

13. A blood pressure measurement method using a display device,
the display device comprising:
a display panel comprising first sub-pixels to emit light of a first color, and second sub-pixels to emit light of a second color;
a pressure sensor to sense a pressure applied from the outside; and
a photo-sensor to sense light,
the method comprising:
generating a first pulse wave signal by sensing, by the photo-sensor, light emitted by the first sub-pixels;
generating a second pulse wave signal by sensing, by the photo-sensor, light emitted by the second sub-pixels;
generating a first pulse wave frequency signal based on the first pulse wave signal, the first pulse wave frequency signal having a magnitude of a pulse wave signal according to a frequency;

generating a second pulse wave frequency signal based on the second pulse wave signal, the second pulse wave frequency signal having a magnitude of a pulse wave signal according to a frequency;

changing the first pulse wave signal based on the first pulse wave frequency signal and the second pulse wave frequency signal;

generating a third pulse wave signal by removing noise from the second pulse wave signal based on the changed first pulse wave signal and the second pulse wave signal; and calculating blood pressure information based on the third pulse wave signal and a pressure measurement value sensed by the pressure sensor, wherein the blood pressure information is displayed on the display panel.

14. The blood pressure measurement method of claim 13, further comprising calculating a first center frequency of first harmonics of the first pulse wave frequency signal, and calculating a second center frequency of second harmonics of the second pulse wave frequency signal, wherein, when the first center frequency and the second center frequency are different from each other, the first pulse wave frequency signal is changed to coincide the first center frequency with the second center frequency.

15. The blood pressure measurement method of claim 14, wherein the generating of the third pulse wave signal comprises:

calculating a first maximum value of the first pulse wave signal;

calculating a second maximum value of the second pulse wave signal; and generating the third pulse wave signal based on a ratio of the second maximum value to the first maximum value.

16. The blood pressure measurement method of claim 15, wherein the third pulse wave signal is generated according to $$PG3 = PG2 - \frac{K2}{K1}PG1,$$

where PG1 is the first pulse wave signal, K1 is the first maximum value, PG2 is the second pulse wave signal, K2 is the second maximum value, and PG3 is the third pulse wave signal.

17. The blood pressure measurement method of claim 13, wherein the calculating of the blood pressure information comprises generating a fifth pulse wave signal based on the third pulse wave signal and the pressure measurement value, wherein one cycle of the fifth pulse wave signal comprises a plurality of waveforms having different amplitudes from one another, a peak value of a first waveform of the plurality of waveforms having a pulse wave contraction value SP, and a peak value of a second waveform of the plurality of waveforms having a reflected pulse wave value, and wherein a reflected pulse wave ratio is defined by $$RI = \frac{Rp}{Sp},$$

where RI is the reflected pulse wave ratio, SP is the pulse wave contraction value, and RP is the reflected pulse wave value.

18. The blood pressure measurement method of claim 17, wherein the reflected pulse wave ratio comprises a first period in which the reflected pulse wave ratio fluctuates within a first range, a second period in which the reflected pulse wave ratio fluctuates within a second range, and a third period in which the reflected pulse wave ratio fluctuates within a third range, and wherein a width of the first range and a width of the third range are smaller than a width of the second range.

19. The blood pressure measurement method of claim 18, wherein:

the reflected pulse wave ratio is analyzed to detect a start point in time of the second period;

a third pressure value corresponding to the first pulse wave signal at the start point in time of the second period is calculated as a diastolic blood pressure; and a fourth pressure value corresponding to the first pulse wave signal at a start point in time of the third period after the second period is calculated as a systolic blood pressure.

20. A display device comprising:

a display panel comprising first sub-pixels to emit light of a first color, and second sub-pixels to emit light of a second color;

a pressure sensor to sense a pressure applied from the outside;

a photo-sensor to sense light; and a main processor to receive a pressure measurement value sensed by the pressure sensor, a first pulse wave signal generated by sensing, by the photo-sensor, light emitted by the first sub-pixels, and a second pulse wave signal generated by sensing, by the photo-sensor, light emitted by the second sub-pixels, wherein the main processor is configured to:

generate a third pulse wave signal by removing noise from the second pulse wave signal based on the first pulse wave signal, the second pulse wave signal, and a maximum value of the first pulse wave signal; and calculate blood pressure information based on the third pulse wave signal and the pressure measurement value.

* * * * *